(12) United States Patent
Benning et al.

(10) Patent No.: US 7,230,160 B2
(45) Date of Patent: Jun. 12, 2007

(54) LIPID METABOLISM REGULATORS IN PLANTS

(75) Inventors: Christoph Benning, East Lansing, MI (US); Alex Cernac, East Lansing, MI (US)

(73) Assignee: Michigan State University, East Lansing, MI (US)

(*) Notice: Subject to any disclaimer, the term of this patent is extended or adjusted under 35 U.S.C. 154(b) by 109 days.

(21) Appl. No.: 10/094,458

(22) Filed: Mar. 8, 2002

(65) Prior Publication Data

US 2003/0097685 A1 May 22, 2003

Related U.S. Application Data

(60) Provisional application No. 60/274,170, filed on Mar. 8, 2001.

(51) Int. Cl.
*A01H 5/00* (2006.01)
*C12N 15/82* (2006.01)

(52) U.S. Cl. .................. 800/281; 800/298; 536/23.6

(58) Field of Classification Search .............. 800/281, 800/298; 536/23.1; 435/320.1, 419
See application file for complete search history.

(56) References Cited

U.S. PATENT DOCUMENTS

| | | | |
|---|---|---|---|
| 5,777,201 A | 7/1998 | Poutre et al. | 800/250 |
| 5,955,650 A | 9/1999 | Hitz | 800/281 |
| 6,084,164 A | 7/2000 | Bidney et al. | 800/322 |
| 6,775,337 B2 * | 8/2004 | Janky et al. | 375/345 |

OTHER PUBLICATIONS

Broun et al, Science 282: 131-133, Nov. 13, 1998.*
Van de Loo et al, PNAS, USA 92: 6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 426-427, Oct. 1996.*
De Luca, V., AgBiotech News and Information 5(6): 225N-229N, 1993.*
EST Database Accession B25031, Rounsley et al, Oct. 10, 1997.*
Bloecker et al., Database GenEmbl, Accession No. AL132971, Nucleic acid Search, Mar. 20, 2000.
Bloecker et al., Database PIR-73, Accession No. T47592 from clone T12E18, Protein Search, Apr. 20, 2000.
Brenner, "Regulatory function of Δ6 desaturase—key enzyme of polyunsaturated fatty acid synthesis", 1977, Adv. Exp. Med. Biol., vol. 83, 85-101.
Cernac et al., "Wrinkled 1 encodes an AP2/EREB domain protein involved in the control of storage compound biosynthesis in Arabidopsis", 2004, The Plant Journal, vol. 40, pp. 575-585.
Hatje et al., "World Importance of Oil Crops and Their Products", Oil Crops of the World-Their Breeding and Utilization, 1989, eds. Röbbelen, Downey, and Ashri, pp. 1-21.

Kinney et al., 1994, "Genetic Modification of the Storage Lipids of Plants, "Current Opin. in Biotech. 5:144-151.
Töpfer., "Modification of Plant Lipid Synthesis", 1995, Science, vol. 268, 681-86.
Bloecker et al., "AIntegumenta-like protein," Accession No. Q9M2V4, retrieved from EBI, Database Uniprot Online Oct. 1, 2000.
White et al., "M26E11XTM Arabidopsis developing seed Arabidopsis thallana clone M26E11 3',mRNA", Accession No. BE522539, retrieved from EBI, Database EMBL Online, Aug. 10, 2000.
White et al., "M26E12STM Arabidopsis developing seed Arabidopsis thaliana cDNA clone M26E125' mRNA," Accession No. BE522540, retrieved from EBI, Database EMBL Online, Aug. 10, 2000.
White et al., "A New Set of Arabidopsis Expressed Sequence Tags from Developing Seeds. The Metabolic Pathway from Carbohydrates to Seed Oil," Plant Physiol., 2000, 124:1582-1594.
Töpfer et al., "Modification of Plant Lipid Synthesis", 1995, Science, vol. 268, 681-86.
Cahoon et al., "Expression of a coriander desaturase results in petroselinic acid production in transgenic tobacco". 1992. Proc. Natl. Acad. Sci. USA, vol 89, 11184-88.
Van de Loo et al., 1993, "Unusual Fatty Acids" in Lipid Metabolism in Plants, ed. Thomas S Moore Jr., CRC Press.
Ohlrogge & Browse, "Lipid Biosynthesis", 1995, Plant Cell, vol. 7, 957-70.
Voelker, 1996. "Plant acyl-ACP Thioesterases: chain-length determining enzymes in plant fatty acid biosynthesis" in Genetic Engineering, ed. Jane K. Setlow, vol. 18, 111-33.
Shanklin & Cahoon, "Desaturation and related modifications of fatty acids", 1998, Annu. Rev. Plant Physiol. Plant Mol. Biol.. vol. 49, 611-641.
Frentzen. "Acyltransferases from basic science to modified seed oils", 1998, Lipid, vol. 100, 161-66.
Van de Loo et al., "An oleate 12-hydroxylase from *Ricinus communis* L. is a fatty acyl desaturase homolog", 1995, Proc. Natl. Acad. Sci. USA, vol. 92, 6743-47.
Brenner, "Regulatory function of Δ6 desaturase—key enzyme of polyunsaturated fatty acid synthesis" 1977, Adv. Exp. Med. Biol., vol. 83, 85-101.
Focks & Benning, "*wrinkled1*: A Novel, Low-Seed-Oil Mutant of Arabidopsis with a Deficiency in the Seed-Specific Regulation of Carbohydrate Metabolism", 1998, Plant Physiol., vol. 118, 91-101.

(Continued)

*Primary Examiner*—Elizabeth F. McElwain
(74) *Attorney, Agent, or Firm*—Connolly Bove Lodge & Hutz LLP

(57) ABSTRACT

The present invention is directed to novel nucleic acid and amino acid sequences associated with the metabolism of seed storage compounds in plants. A novel discovery described herein lies in the identification of the nucleic acid sequences that encode the wri1 genetic locus in *Arabidopsis thaliana*, and lipid metabolism regulator (LMR) polynucleotide sequences contained therein. Preferably, the seed storage compounds are lipids, fatty acids, starches or seed storage proteins.

26 Claims, 11 Drawing Sheets

OTHER PUBLICATIONS

The Arabidopsis Genome Initiative 2000 Analysis of the genome sequence of the flowering plant *Arabidopsis thaliana*. Nature 408:796-844.

Meyer et al., "A protein phosphatase 2C involved in ABA signal transduction in *Arabidopsis thaliana*", 1994, Science 264:1452-55.

* cited by examiner

Diagram illustrating the complementation of the *wri1* Arabidopsis mutant with wild type cosmid clones

FIGURE 3

Sequence alignment of an LMR protein sequence (WRI1, SEQ ID NO:3) and LMR candidate sequences SEQ ID NO:8 and SEQ ID NO:9

Name: WRI1 SEQ ID NO:3           Length: 430
Name: WRI1 Candidate SEQ ID NO:8  Length: 205
Name: WRI1 Candidate SEQ ID NO:9  Length: 221

```
             1                                                      50
WRI1    MKKRLTTSTC SSSPSSSVSS STTTSSPIQS EAPRPKRAKR AKKSSPSGDK
Seq_8   MKKRLTTSTC SSSPSSSVSS STTTSSPIQS EAPRPKRAKR AKKSSPSGDK
Seq_9   .......... .......... .......... .......... ..........

51                                                    100
WRI1    SDNPTSPAST RRSSIYRGVT RHRWTGRFEA HLWDKSSWNS IQNKKGKQVY
Seq_8   SHNPTSPAST RRSSIYRGVT RHRWTGRFEA HLWDKSSWNS IQNKKGK...
Seq_9   .......... .......... .......... .......... ..........

101                                                   150
WRI1    LGAYDSEEAA AHTYELAALK YWGPDTILNF PAETYTKELE EMQRVTKEEY
Seq_8   QGAYDSEEAA AHTYDLAALK YWGPDTILNF PAETYTKELE EMQRVTKEEY
Seq_9   .......... .......... .......... .......... ..........

151                                                   200
WRI1    LASLRRQSSG FSRGVSKYRG VARHHHNGRW EARIGRVFGN KYLYLGTYNT
Seq_8   LASLRRQSSG FSRGVSKYRG VARHHHNGRW EARIGRVFGN KYLYLGTYST
Seq_9   .......... .......... .......... .......... ..........

201                                                   250
WRI1    QEEAAAAYDM AAIEYRGANA VTNFDISNYI DRLKKKGVVP FPVNQAKDQE
Seq_8   LSPFPFFF.. .......... .......... .......... ..........
Seq_9   .........M AAIEYRGANA VTNFDISNYI DRLKKKGVFP FPVNQANHQE
```

FIGURE 3 CONTINUED

```
        251                                                      300
WRI1    GILVEAKQEV ETREAKEEPR EEVKQQYVEE PPQEEEEKEE EKAEQQEAEI
Seq_8   .......... .......... .......... .......... ..........
Seq_9   GILVEAKQEV ETREAKEEPR EEVKQQYVEE PPQEEEEKEE EKAEQQEAEI 301                                                      350
WRI1    VGYSEEAAVV ICCIDSSTIM EMDRCGDNNE LAWNFCMMDT GFSPFLTDQN
Seq_8   .......... .......... .......... .......... ..........
Seq_9   VGYSEEAAVV NCCIDSSTIM EMDRCGDNNE LAWNFCMMDT GFSPFLTDQN 351                                                      400
WRI1    LANENPIEYP ELFLELAFED NIDFMFDDGK HECLNLELLD CCVVGRESPP
Seq_8   .......... .......... .......... .......... ..........
Seq_9   LANENPIEYP ELFNELAFED NIDFMFDDGK HECLNLENLD CCVVGRESPP 401                      430
WRI1    SSSSPLSCLS TDSASSTTTT TTSVSCNYLV
Seq_8   .......... .......... ..........
Seq_9   SSSSPLSCLS TDSASSTTTT TTSVSCNYLV
```

FIGURE 4A

Nucleotide sequence of a LMR cDNA from *Arabidopsis thaliana* (SEQ ID NO:1)

```
AAACCACTCTGCTTCCTCTTCCTCTGAGAAATCAAATCACTCACACTCCAAAAAAAA
ATCTAAACTTTCTCAGAGTTTAATGAAGAAGCGCTTAACCACTTCCACTTGTTCTTCT
TCTCCATCTTCCTCTGTTTCTTCTTCTACTACTACTTCCTCTCCTATTCAGTCGGAGGC
TCCAAGGCCTAAACGAGCCAAAAGGGCTAAGAAATCTTCTCCTTCTGGTGATAAATC
TCATAACCCGACAAGCCCTGCTTCTACCCGACGCAGCTCTATCTACAGAGGAGTCAC
TAGACATAGATGGACTGGGAGATTCGAGGCTCATCTTTGGGACAAAAGCTCTTGGA
ATTCGATTCAGAACAAGAAAGGCAAACAAGTTTATCTGGGAGCATATGACAGTGAA
GAAGCAGCAGCACATACGTACGATCTGGCTGCTCTCAAGTACTGGGGACCCGACAC
CATCTTGAATTTTCCGGCAGAGACGTACACAAAGGAATTGGAAGAAATGCAGAGAG
TGACAAAGGAAGAATATTTGGCTTCTCTCCGCCGCCAGAGCAGTGGTTTCTCCAGAG
GCGTCTCTAAATATCGCGGCGTCGCTAGGCATCACCACAACGGAAGATGGGAGGCT
CGGATCGGAAGAGTGTTTGGGAACAAGTACTTGTACCTCGGCACCTATAATACGCA
GGAGGAAGCTGCTGCAGCATATGACATGGCTGCGATTGAGTATCGAGGCGCAAACG
CGGTTACTAATTTCGACATTAGTAATTACATTGACCGGTTAAAGAAGAAAGGTGTTG
TCCCGTTCCTGTGAACCAAGCTAAGGATCAAGAGGGTATTCTTGTTGAAGCCAAAC
AAGAAGTTGAAACGAGAGAAGCGAAGGAAGAGCCTAGAGAAGAAGTGAAACAACA
GTACGTGGAAGAACCACCGCAAGAAGAAGAAGAGAAGGAAGAAGAGAAAGCAGA
GCAACAAGAAGCAGAGATTGTAGGATATTCAGAAGAAGCAGCAGTGGTCAATTGCT
GCATAGACTCTTCAACCATAATGGAAATGGATCGTTGTGGGACAACAATGAGCTG
GCTTGGAACTTCTGTATGATGGATACTGGGTTTTCTCCGTTTTGACTGATCAGAATC
TCGCGAATGAGAATCCCATAGAGTATCCGGAGCTATTCAATGAGTTAGCATTTGAGG
ACAACATCGACTTCATGTTCGATGATGGGAAGCACGAGTGCTTGAACTTGGAAAATC
TGGATTGTTGCGTGGTGGGAAGAGAGAGCCCACCCTCTTCTTCTTCACCATTGTCTTG
CTTATCTACTGACTCTGCTTCATCAACAACAACAACAACAACCTCGGTTTCTTGTAAC
TATTTGGTCTGAGAGAGAAGAGCTTTGCCTTCTAGTTTGAATTTCTATTTCTTCCGCT
TCTTCTTCTTTTTTTTCTTTTGTTGGGTTCTGCTTAGGGTTTGTATTTCAGTTTCAGGG
CTTGTTCGTTGGTTCTGAATAATCAATGTCTTTGCCCCTTTTCTAATGCTCCAAGTTC
AGAT
```

FIGURE 4B

Nucleotide sequence of the open reading frame of a LMR cDNA from *Arabidopsis thaliana* (SEQ ID NO:2)

ATGAAGAAGCGCTTAACCACTTCCACTTGTTCTTCTTCTCCATCTTCCTCTGTTTCTTC
TTCTACTACTACTTCCTCTCCTATTCAGTCGGAGGCTCCAAGGCCTAAACGAGCCAA
AAGGGCTAAGAAATCTTCTCCTTCTGGTGATAAATCTCATAACCCGACAAGCCCTGC
TTCTACCCGACGCAGCTCTATCTACAGAGGAGTCACTAGACATAGATGGACTGGGA
GATTCGAGGCTCATCTTTGGGACAAAAGCTCTTGGAATTCGATTCAGAACAAGAAA
GGCAAACAAGTTTATCTGGGAGCATATGACAGTGAAGAAGCAGCAGCACATACGTA
CGATCTGGCTGCTCTCAAGTACTGGGGACCCGACACCATCTTGAATTTTCCGGCAGA
GACGTACACAAAGGAATTGGAAGAAATGCAGAGAGTGACAAAGGAAGAATATTTG
GCTTCTCTCCGCCGCCAGAGCAGTGGTTTCTCCAGAGGCGTCTCTAAATATCGCGGC
GTCGCTAGGCATCACCACAACGGAAGATGGGAGGCTCGGATCGGAAGAGTGTTTGG
GAACAAGTACTTGTACCTCGGCACCTATAATACGCAGGAGGAAGCTGCTGCAGCAT
ATGACATGGCTGCGATTGAGTATCGAGGCGCAAACGCGGTTACTAATTTCGACATTA
GTAATTACATTGACCGGTTAAAGAAGAAAGGTGTTGTCCCGTTCCCTGTGAACCAAG
CTAAGGATCAAGAGGGTATTCTTGTTGAAGCCAAACAAGAAGTTGAAACGAGAGAA
GCGAAGGAAGAGCCTAGAGAAGAAGTGAAACAACAGTACGTGGAAGAACCACCGC
AAGAAGAAGAAGAGAAGGAAGAAGAGAAAGCAGAGCAACAAGAAGCAGAGATTG
TAGGATATTCAGAAGAAGCAGCAGTGGTCAATTGCTGCATAGACTCTTCAACCATAA
TGGAAATGGATCGTTGTGGGGACAACAATGAGCTGGCTTGGAACTTCTGTATGATGG
ATACTGGGTTTTCTCCGTTTTTGACTGATCAGAATCTCGCGAATGAGAATCCCATAG
AGTATCCGGAGCTATTCAATGAGTTAGCATTTGAGGACAACATCGACTTCATGTTCG
ATGATGGGAAGCACGAGTGCTTGAACTTGGAAAATCTGGATTGTTGCGTGGTGGGA
AGAGAGAGCCCACCCTCTTCTTCTTCACCATTGTCTTGCTTATCTACTGACTCTGCTT
CATCAACAACAACAACAACAACCTCGGTTTCTTGTAACTATTTGGTCTGA

FIGURE 4C
Amino acid sequence of a LMR protein from *Arabidopsis thaliana* (SEQ ID NO:3)

MKKRLTTSTCSSSPSSSVSSSTTTSSPIQSEAPRPKRAKRAKKSSPSGDKSHNPTSPASTRR
SSIYRGVTRHRWTGRFEAHLWDKSSWNSIQNKKGKQVYLGAYDSEEAAAHTYDLAAL
KYWGPDTILNFPAETYTKELEEMQRVTKEEYLASLRRQSSGFSRGVSKYRGVARHHHN
GRWEARIGRVFGNKYLYLGTYNTQEEAAAAYDMAAIEYRGANAVTNFDISNYIDRLKK
KGVVPFPVNQAKDQEGILVEAKQEVETREAKEEPREEVKQQYVEPPQEEEEKEEEKAE
QQEAEIVGYSEEAAVVNCCIDSSTIMEMDRCGDNNELAWNFCMMDTGFSPFLTDQNLA
NENPIEYPELFNELAFEDNIDFMFDDGKHECLNLENLDCCVVGRESPPSSSSPLSCLSTDS
ASSTTTTTSVSCNYLV

FIGURE 5A

Nucleotide sequence of a LMR cDNA from *Arabidopsis thaliana* (SEQ ID NO:4)

```
TTGGTACCAAATCTAAACTTTCTCAGAGTTTAATGAAGAAGCGCTTAACCACTTCCA
CTTGTTCTTCTTCTCCATCTTCCTCTGTTTCTTCTTCTACTACTACTTCCTCTCCTATTC
AGTCGGAGGCTCCAAGGCCTAAACGAGCCAAAAGGGCTAAGAAATCTTCTCCTTCT
GGTGATAAATCTCATAACCCGACAAGCCCTGCTTCTACCCGACGCAGCTCTATCTAC
AGAGGAGTCACTAGACATAGATGGACTGGGAGATTCGAGGCTCATCTTTGGGACAA
AAGCTCTTGGAATTCGATTCAGAACAAGAAAGGCAAACAAGTTTATCTGGGAGCAT
ATGACAGTGAAGAAGCAGCAGCACATACGTACGATCTGGCTGCTCTCAAGTACTGG
GGACCCGACACCATCTTGAATTTTCCGGCAGAGACGTACACAAAGGAATTGGAAGA
AATGCAGAGAGTGACAAAGGAAGAATATTTGGCTTCTCTCCGCCGCCAGAGCAGTG
GTTTCTCCAGAGGCGTCTCTAAATATCGCGGCGTCGCTAGGCATCACCACAACGGAA
GATGGGAGGCTCGGATCGGAAGAGTGTTTGGGAACAAGTACTTGTACCTCGGCACC
TATAATACGCAGGAGGAAGCTGCTGCAGCATATGACATGGCTGCGATTGAGTATCG
AGGCGCAAACGCGGTTACTAATTTCGACATTAGTAATTACATTGACCGGTTAAAGAA
GAAAGGTGTTTTCCCGTTCCCTGTGAACCAAGCTAACCATCAAGAGGGTATTCTTGT
TGAAGCCAAACAAGAAGTTGAAACGAGAGAAGCGAAGGAAGAGCCTAGAGAAGAA
GTGAAACAACAGTACGTGGAAGAACCACCGCAAGAAGAAGAAGAGAAGGAAGAAG
AGAAAGCAGAGCAACAAGAAGCAGAGATTGTAGGATATTCAGAAGAAGCAGCAGT
GGTCAATTGCTGCATAGACTCTTCAACCATAATGGAAATGGATCGTTGTGGGGACAA
CAATGAGCTGGCTTGGAACTTCTGTATGATGGATACAGGGTTTTCTCCGTTTTTGACT
GATCAGAATCTCGCGAATGAGAATCCCATAGAGTATCCGGAGCTATTCAATGAGTTA
GCATTTGAGGACAACATCGACTTCATGTTCGATGATGGGAAGCACGAGTGCTTGAAC
TTGGAAAATCTGGATTGTTGCGTGGTGGGAAGAGAGAGCCCACCCTCTTCTTCTTCA
CCATTGTCTTGCTTATCTACTGACTCTGCTTCATCAACAACAACAACAACAACCTCG
GTTTCTTGTAACTATTTGGTCTGAGAGAGAGAGCTTTGCCTTCTAGTTTGAATTTCTA
TTTCTTCCGCTTCTTCTTCTTTTTTTCTTTTGTTGGGTTCTGCTTAGGGTTTGTATTTC
AGTTTCAGGGCTTGTTCGTTGGTTCTGAATAATCAATGTCTTTGCC
```

FIGURE 5B

Nucleotide sequence of the open reading frame of a LMR cDNA from *Arabidopsis thaliana* (SEQ ID NO:5)

ATGAAGAAGCGCTTAACCACTTCCACTTGTTCTTCTTCTCCATCTTCCTCTGTTTCTTC
TTCTACTACTACTTCCTCTCCTATTCAGTCGGAGGCTCCAAGGCCTAAACGAGCCAA
AAGGGCTAAGAAATCTTCTCCTTCTGGTGATAAATCTCATAACCCGACAAGCCCTGC
TTCTACCCGACGCAGCTCTATCTACAGAGGAGTCACTAGACATAGATGGACTGGGA
GATTCGAGGCTCATCTTTGGGACAAAAGCTCTTGGAATTCGATTCAGAACAAGAAA
GGCAAACAAGTTTATCTGGGAGCATATGACAGTGAAGAAGCAGCAGCACATACGTA
CGATCTGGCTGCTCTCAAGTACTGGGGACCCGACACCATCTTGAATTTTCCGGCAGA
GACGTACACAAAGGAATTGGAAGAAATGCAGAGAGTGACAAAGGAAGAATATTTG
GCTTCTCTCCGCCGCCAGAGCAGTGGTTTCTCCAGAGGCGTCTCTAAATATCGCGGC
GTCGCTAGGCATCACCACAACGGAAGATGGGAGGCTCGGATCGGAAGAGTGTTTGG
GAACAAGTACTTGTACCTCGGCACCTATAATACGCAGGAGGAAGCTGCTGCAGCAT
ATGACATGGCTGCGATTGAGTATCGAGGCGCAAACGCGGTTACTAATTTCGACATTA
GTAATTACATTGACCGGTTAAAGAAGAAAGGTGTTTTCCCGTTCCCTGTGAACCAAG
CTAACCATCAAGAGGGTATTCTTGTTGAAGCCAAACAAGAAGTTGAAACGAGAGAA
GCGAAGGAAGAGCCTAGAGAAGAAGTGAAACAACAGTACGTGGAAGAACCACCGC
AAGAAGAAGAAGAGAAGGAAGAAGAGAAAGCAGAGCAACAAGAAGCAGAGATTG
TAGGATATTCAGAAGAAGCAGCAGTGGTCAATTGCTGCATAGACTCTTCAACCATAA
TGGAAATGGATCGTTGTGGGGACAACAATGAGCTGGCTTGGAACTTCTGTATGATGG
ATACAGGGTTTTCTCCGTTTTTGACTGATCAGAATCTCGCGAATGAGAATCCCATAG
AGTATCCGGAGCTATTCAATGAGTTAGCATTTGAGGACAACATCGACTTCATGTTCG
ATGATGGGAAGCACGAGTGCTTGAACTTGGAAAATCTGGATTGTTGCGTGGTGGGA
AGAGAGAGCCCACCCTCTTCTTCTTCACCATTGTCTTGCTTATCTACTGACTCTGCTT
CATCAACAACAACAACAACAACCTCGGTTTCTTGTAACTATTTGGTCTGA

FIGURE 5C

Amino acid sequence of a LMR protein from *Arabidopsis thaliana* (SEQ ID NO:6)

MKKRLTTSTCSSSPSSSVSSSTTTSSPIQSEAPRPKRAKRAKKSSPSGDKSHNPTSPASTRR
SSIYRGVTRHRWTGRFEAHLWDKSSWNSIQNKKGKQVYLGAYDSEEAAAHTYDLAAL
KYWGPDTILNFPAETYTKELEEMQRVTKEEYLASLRRQSSGFSRGVSKYRGVARHHHN
GRWEARIGRVFGNKYLYLGTYNTQEEAAAAYDMAAIEYRGANAVTNFDISNYIDRLKK
KGVFPFPVNQANHQEGILVEAKQEVETREAKEEPREEVKQQYVEEPPQEEEEKEEEKAE
QQEAEIVGYSEEAAVVNCCIDSSTIMEMDRCGDNNELAWNFCMMDTGFSPFLTDQNLA
NENPIEYPELFNELAFEDNIDFMFDDGKHECLNLENLDCCVVGRESPPSSSSPLSCLSTDS
ASSTTTTTSVSCNYLV

FIGURE 6

Truncated nucleic acid sequence of BAC clone T12E18 (Genbank accession AL132971) (SEQ ID NO:7)

```
AAGCTTCAATATGATTCACTTAAAATGTGGTAAGTAGGGGAGATGAAAAGGACTTA
TCTTATAGAAATTGAGTCGTTTATTTTGTTGGTCCACCATACATTTACATGAAATGGT
TACATCAGGACGAGTGTTGTCTGAGACCTAGAAAATCAGAAACCAAAACCACAAAA
GAATTAAAATGAAATTACAGACACAATCATGAATCTCTAACATAAGAAATAACAAA
ACCACCTTCACGTGATACAACTCTTTGGTTTCTTCAACACAAAATCCCATTTTGTGTA
CAGCTCTATACCCAACATTTTCGACATAAGACTTTGGGACATTTGTACGAAACATTT
TCTTCAATTTCTCCAAAGTGCTTTTAGTTAACGGACCATCTCTTAGAGTTCCTGATGA
ACTAACACTGCATCAATTTGATAAGATAACAATCGGTAAACTTGTTTATTCAACATA
AAAAAGACTTGATTAGCGAGAAATGCGCAATCCAACTATAGTTTCTAAGTTGTCTAG
ATAGTAGATAACCGACTCAACTATAGTGTCCAAGTTGTCAACACAGTTTCAATCCAC
TACAAACCACCTACGGTAATTACAATGCTCTTAAACCAACACTAGGCTAATCACTAA
CCCTGCCCCAGGTAAAACAGAGTTTGTGTGTGTCCCTAAAAACTGAAAATTTGAGGA
GAAGTCAAAAACCTTACTCATGGAAAACAACATTACCAAACCGAGCGATCAGTCTG
AGTTTGACATCCTCTGATCCACCATAACCTAGCAACGTCTTCTTTGCCCTATCAAATC
CCATTATAATGTCATCCTCCACTTTCTCTGTCACCCATAACCATGGATTTTCCAGTTT
TCCCAAATCACTCTTCGCTAAGATTACCAAAGATTTTTCTTCTGCGTCTTTCCTCCAC
TCTGAAGAACCGGGCACAAGTTGAAAGTTGCTATCCTCTGGATCCGAACCAACGAG
AAACCATCTAGAAATGTAACCGTTTGCGTAGATTATCTTTGTATTAGTACTCCCGAC
GTTTTTATTGTGTTTTTAAGAAGAGAAGGTGGAACAGAGGATGCTCTCAATGCAAC
ATTTTCAAGTCGTTTATGTGGTGGAACGTAAGACATCTCTGAAACGAATATATGATA
CTAGGAAAATTAAAAGCTGATTCCAAAAAGATAACTCAAGTTTCCGAGCAACGAAG
TATGAGAAGAAGAAACAAAAGAGTACCTTTTAATTATATCAGCTTAGGTCATTCAAA
AGAAGAACGACGATCATACGAGAGGAAACTGAAAAGGCGCAGAGCAGTGAACTGA
AGTGGAAGAGACGAGACGGTTTGGTCTTTTTATCACTAGAAGTTTAGTCTTGGAAAT
GTGCATAATATTTAATTTCATTTCAATTTTCAAATCAAAAAATAAAACCGATAACGA
AACTCTTGTTATCATATTATGAGCGTTGATAATTTAGAGAATCTCTGTTCTTTTAGAA
AATTGTATGAACATTTTGTTAAATAAATAACTATTTTAAATGCTAAACCTCATTGTT
TAGTCCTAAATGTTAGGAATCTTAGTATTCATTTTTTTTCCTCTTATGATATACACTT
CCGGTTTAGATTTCTAGGACGTTTTAAATTTAATTATTACTGCTAATAAAAATAGTTA
TTTATTTTAAACAATTAAATAAAACAATTGTATCTCTAGAGTAAAAAAAGTTTTAA
AAATTTGGTGAATGTTTTATTTGGCAACCCAACTTAATTCCTGAAACGAATCACG
AGAATTATTTAACGTACTACAAAAGGTACATCTAATTTCTAAAACCGAATTAGACT
ATCGTCTTGGTTGTTTTGGATGTTGCATGTCTATATTATGATAATTATTCTGTAAGC
ATTACAATTAAATCGTTTCTGTTTTACTAAAGGAGTTTTGACTGTTTTAAACGACTG
TAAACACTCGTGTGTCTGCTTAAATCATGTGGAAAGTTAAATGATAACAGTTAGAAC
ATCCAACTTTACATATGCTTTGATTAGACATTTCTACGATATGTTCGGATTGACAC
GTGCTAATCATATCTGATCATTTTCCCATTTTACATATGTTCTAATTAGGCATTTTCG
ACGATACATTTTAGATCGATAATGTGTTAATAATCATCTGACATTTTTACTTTGTAT
GTTCTAATTATGTATTTATACGATAAACATTAGATCGACACATGCAAAACATTCGAC
AATTTGTTGAACACTGAAGACCTAATTTGGTATAATACAGCTCAGCGAAGATACGTT
ACAACTAATTTGGAGCGTTTATAGAAAATATAGGCAAATAGCCAAATATGCTAATA
AAAAGATTTAGAACTTTAATAGGTAATTTAACACATTTTATAACACACAAGCATATA
```

FIGURE 6 CONTINUED

```
TATTTAAAAGGGAAAAAACTAGTCAACTTTCATAGACCATCATTACCATAATAACTC
AATTCAATCAAATTTTAATTTTTGGCTACTATTTTTCTTTTCTAAAACCAAAACATCA
TCATAGTAGATTCTTCAATTTTAAAATATAGAATTCAAATTGTTGACCAGGGAATAA
ATAGAATTGCAAAAAAACAAATTAAGATATTTTACATTCCAACTTTTCCCCCAAAAA
ATTAGAGAAAAAAATCAAATTAAATTCAATAATTCCAAAACATAAAACGTACAAAA
AAGTTAATGATAAAAAAACGTAAAAAAAAATACAAAAATACAAAGAAAAAGAAA
GACAGCGTGGAGAGTAAAGCTATTGGTAGCATGGCTGCAACAGAAGGCCAAGTGTT
TGGTCTTACAATTTCATTTTTAACTCTTTGTGTTAATTAACCCAATTAGCCCTTTCCTC
CTTCAGGGTTTATTTAACTTGCCCTTTCTCGTTCCTCCTTTTTTCTTAAACCACTCT
GCTTCCTCTTCCTCTGAGAAATCAAATCACTCACACTCCAAAAAAAAATCTAAACTT
TCTCAGAGTTTAATGAAGAAGCGCTTAACCACTTCCACTTGTTCTTCTTCTCCATCTT
CCTCTGTTTCTTCTTCTACTACTACTTCCTCTCCTATTCAGTCGGAGGCTCCAAGGCCT
AAACGAGCCAAAAGGGCTAAGAAATCTTCTCCTTCTGGTGATAAATCTCATAACCCG
ACAAGCCCTGCTTCTACCCGACGCAGCTCTATCTACAGAGGAGTCACTAGGTTTTTA
TTTTTTTGGAAATTAAATGATTGGTTGTTGAGATTGGATTTGGGTTTTGTCTTAAAAC
TGCATTTGTAAGATTGCATGTTGTTTTGTGGGATTTTGCAGACATAGATGGACTGGG
AGATTCGAGGCTCATCTTTGGGACAAAAGCTCTTGGAATTCGATTCAGAACAAGAA
AGGCAAACAAGGTTTCGTCTTCTTCTTTTTTCTTCGTAACTCATGATTTGTTTGTTT
TAATAAAGATCTGGACTTTAACTGATAAATTTGGTTTCTTTGATCTGTTGTTTGATCT
CAACTTCGTCACAACTTCACCAGTTTATCTGGGTAAGCTCTAATTCTCTGAAACAAA
AGATCAATTGTTTTTTACTAAATTGAAAGAGAAAAAAAAAGAGAGAGTGGATTTGG
TCAGAAGAATCTCAACTGCTTTCACGCGTAATTGCAGGAGCATATGACAGTGAAGA
AGCAGCAGCACATACGTACGATCTGGCTGCTCTCAAGTACTGGGGACCCGACACCA
TCTTGAATTTTCCGGTAAACCAAAAAACAAAAATCAGATTGTTTTGATATGCATGTT
TGTGATTTTGGAATCTGGATTATAATTAAAAAAAAAAATGGGGAAAATCAGGCAGA
GACGTACACAAAGGAATTGGAAGAAATGCAGAGAGTGACAAAGGAAGAATATTTG
GCTTCTCTCCGCCGCCAGAGCAGTGGTTTCTCCAGAGGCGTCTCTAAATATCGCGGC
GTCGCTAGGTTCCTTTTTTTCTCTCTTTCTTTTTTAATTTCTTTAGATTTATTTTTAA
ATTTCGGAATTTACTACCAAATTGAGAAATGATTTTTCCTATTTCGGATATCTGAAT
AACAGAATTAATTATTAGGAAAAAATCTGATCATGAAAATTTTGCTTTTAGAATATT
CTCTTTTTCTTAAAAAAAATCATAAATTATGTTTTTTTCAGCACTGCTAAAGTTTATG
GATTCAATAGTTTGGTCATTTTATTCTTAAAAATAGGATTATTTTTGTTCATAAAAAC
AGGCATCACCACAACGGAAGATGGGAGGCTCGGATCGGAAGAGTGTTTGGGAACAA
GTACTTGTACCTCGGCACCTATAGTACGTTATCTCCTTTCCCTTTTTCTTCTAGTAAT
TTTTAGAAAAAAATAGATATGTACTCTTGGTTAATTTAAAATAATTAGCGTAATTAT
TGACTTTTTTATAACTTACCGGGCATAACGGATCCTTTTTACCTGTTATGCTTTATAA
TATATAATTTTGTAAGTATAAAATAGAGTGTGATAATGTTTAGACTGTTTTTTGTTGT
TGTTTATAAGAGTGATTTAAGAATATTAATTTGTTTAGTGAGACAATTAGAATAATA
TAATGGGGAAGCAGTGGCAGTGGGGTTTGAATTTTACACACACTGACTCACGTGAG
GCGAGAGTTTTGACATCATGTCCCTTTAATTGATTTTATCTTTTAATCAAATCAACT
TTTTTCTTCTTCTTTTTAATTATCTGATCCCTCTGCATAATTACCTTTTAAATTCTGC
ATTTTTTGTGGATCCGATACTCTGAATACAAAAATTGAGAACTCTGCAGAAGGGAAT
ATTAACAACAACTCTTTTACTGAAAAGTAATCCCATTTTTTTTATTGTTTTGCTGA
CTCTTACCGGGTCCTTAGATTTATTTAAGGACCTCCTAATCTTCAACAAATCTCAAAT
TTTTGAAAATTAGATTTTTTTAAAAAAGTAATACAAATTGAGATTTGCAAAAATATA
GGCATTGTTGTTCTATAACAAAGATACTTTATTTATACCAAAAAAAAGAAAAGAGTT
GTCAAGAGCATAATTACAAAAAAAAAAATTGAAATAAGTAGTAGTTGTGAAATTTT
```

FIGURE 6 CONTINUED

```
GTATAGAAAAATAATGTAGGTTACAAGTGTAAAGGCGCGTGTAGCGCGCGTAGGTC
ACGTGATAACACTCTCACTTCATAAAAGGACAAAATAGTTCAGAGAGGCTTTAGGA
CCAAACCCGAGGTCGATCTGGTTTGCTCTTGTTTTTTGGTTTATTAAATTGGATTAA
TTAGTTAGAGTTGAGACTTGCTCTGAGTAGGAGTCACGAGCCCTCACGTGCACTGCT
CATCTCTCTCTATCTCTCTACCATATCTTTCATCTTTGTCCTCCGAACAAAATCTGGTC
TAACTTTATCTTCTTTTCTTTTAATAATTGTCTTCTCTACTTTACCATTATTTTCTCTA
GATTATTCTGGTACCAAACTTATAACTTAATAGTTGATTAGTGCTTAGAGTTGACACT
AGGTTGGTGTTTTAATTATTGTTAATTAACTCAGTAATCGTACGTTCGTGTATTAATT
ATATACACAAATTGTTGCGATGACTTAAATTAAGTCACAAGTTTGGACTCTTTAGTG
TTTAGAGCGGCGCAGTGGAGGAGAAATGGTCTTTGTACACGCCTCACATCTCCACAC
AAATCGTGTAACCCTAGTTGTCCCTACAAAAACACGTCACCAAATTCTATTGATTCT
TTGTCTTTATTAGGTATCATAAATTCTCTAATTTAAATATGAAACGACAAAGAAGAA
ACTCTTCTTTTAACACTTGTTTGGTCTTATTTGGTTATAGCCACTTACCAGGTAATGT
GAAAGTTAACAACAAGTTGCGTTAACTTTCAAAACACTGACTTTGTTTGCATTGTCTT
GATTTAGAAGCTTTTTAGCTAACACAGTTGTCTATTTATTGGTTTTACAGATACGCAG
GAGGAAGCTGCTGCAGCATATGACATGGCTGCGATTGAGTATCGAGGCGCAAACGC
GGTTACTAATTTCGACATTAGTAATTACATTGACCGGTTAAAGAAGAAAGGTGTTTT
CCCGTTCCCTGTGAACCAAGCTAACCATCAAGAGGGTATTCTTGTTGAAGCCAAACA
AGAAGTTGAAACGAGAGAAGCGAAGGAAGAGCCTAGAGAAGAAGTGAAACAACAG
TACGTGGAAGAACCACCGCAAGAAGAAGAAGAGAAGGAAGAAGAGAAAGCAGAG
CAACAAGAAGCAGAGATTGTAGGATATTCAGAAGAAGCAGCAGTGGTCAATTGCTG
CATAGACTCTTCAACCATAATGGAAATGGATCGTTGTGGGGACAACAATGAGCTGG
CTTGGAACTTCTGTATGATGGATACAGGGTTTTCTCCGTTTTGACTGATCAGAATCT
CGCGAATGAGAATCCCATAGAGTATCCGGAGCTATTCAATGAGTTAGCATTTGAGG
ACAACATCGACTTCATGTTCGATGATGGGAAGCACGAGTGCTTGAACTTGGAAAATC
TGGATTGTTGCGTGGTGGGAAGAGAGAGCCCACCCTCTTCTTCTTCACCATTGTCTTG
CTTATCTACTGACTCTGCTTCATCAACAACAACAACAACAACCTCGGTTTCTTGTAAC
TATTTGGTCTGAGAGAGAGAGCTTTGCCTTCTAGTTTGAATTTCTATTTCTTCCGCTT
CTTCTTCTTTTTTTTCTTTTGTTGGGTTCTGCTTAGGGTTTGTATTTCAGTTTCAGGGC
TTGTTCGTTGGTTCTGAATAATCAATGTCTTTGCCCCTTTTCTAATGCTCCAAGTTCA
GATAAGAAATAAAAACTAAATGAACCGTAAAACACAAAGGAGGCTAAGATGTCTAT
GAATTTCTCTGGCATATGTGCAATAAGGAAGAGCTTCAAGGAATCTTGAACTAAGA
GAAGGCTTCAAAGGCTAGACCTCTTCAAGTTCCCCTGTCTTATTATTGACCGGACTA
TGAAGTTTCTAGGAAGGTTATATAGGCAAAGTTTATTCCTAACTCTTAATTCATAA
TTCTGATTGCGATGATTTTGGTTTGCTAGATAGTTTAGTAAAAGAGCCTTACCATCC
AAACTTGTGATCAATATTGGTAACCGTGAACGTCTTCATTAGGGTGAATATTTGAAT
ATCTTTGTTTTCGGGTTACACATAACAACCCGAAAAGTTGTTGCATTTGGCTCGGAA
TACATCTTGTATAAAAATTTGTCTTTACTTTTTAGTTTTGTAAATCAATAGTATGATT
GGTAGTCTATTCGTTTGTGGAAACAACTTCAATTTGTATTTCATCAGACAATATATA
TGCATTCAAGTAGAAAATCAAATCGAGTAAATTTGTAGCATAATTAAGTAGAGTGGT
CAATATAATAATACGATACATGATAAAAGTCTTGAAAACATTCCACACACAATAAG
CCTAAGCACTACTGATCACACAATCCATATTTCTTTAGGCTTTAAAATACATAACTA
AGAAACATGACAGTTTAAGGTTTTAGCAACACCATGCCTTATGTTTTAAGTAGTTAC
TAAATAATTAGATAGACAATGATGGCACCAGCAAACCTTTTAGCCTTTAATTATTCA
AGAAGATGGAAGGTAATGATGTCAGAGGCAGAGGGTGCATGAAGGCCATGGTTGG
GGTAATAGTGGTGATGGTTCTGGTGGAAACGAAGAGCGTAAGCACGTGACCCTTCG
ATTTGGTATCCAAGAACTGAGTCGTAATCTCCTCCATTGTCTACTAGTCCATAGTGA
```

FIGURE 6 CONTINUED

```
GGATCTTCAGCTCTTAGTTCCTAATTCACCAAAACATGTTTTAAGCCATATTCCACAT
AACTAAAACCAATATTATTAATTCGAAATGACATGACATTTGATATATGATTTAACT
AGGAGATATTTCGATAAGAGAATCACAAGAAAACATAAGAGTGACTGATCAATCTA
CACTACATTTCTAGATATCTTTTTAACTGGCTCCGTATTCCATGAATGTATTATGCCT
AAACCAACATTTGAGAAAACAGAAAGAGATATTACCAGCTCATGTATGAGATTCT
TTTGTATGTCTTGTTGACTTTTGTTCTGCAATTGTGTAAACCACAAGAGAAATGATGA
AGAAATATTCCCTCCCAAAAAAATTATGAAGATATATACCCAAGTTATTATGACATC
ACTATATAGTATACTTGGTATTTTCTTTATCCATTAGCTTAAACACACACACACAC
ACAAATATAATTGTCCAAGAAAAGTGTTATCAACAGTTTTAGTAAGTTGATAAATTC
AATTGACACAAAATTGTTGAGACAAATAAATATGATAAATGGAAAGTGAGTGGA
CATAGAAGATGTGACCTTTTCTTGGTGGTCTCGATCTGATTCCCAAGAGATTTGAA
CTGTACAGTACAATACAATTAACATATATTATCCAACAGTAAACAAAATGTTTCTTT
TTCTAAAACATATATACAACAATAAAATTCATTTTTAATAATTCAATTCAAAACTG
AAGCTTGGGTATATAGGATTAATTGAAACCCTAGGTAAGGGAAAAGTATGAAGAGA
ACCTTGCGCTCGCGAACGAGTTTGAAAGTGTTTCCATTTCATCCTCAAGACGACGC
AGCTCCTGAATGTCAAGCTCGTCCAAACACTCACCTAGCCTCTGCCTACAATTTTAA
AAATATGTATATTTTCGTACTCATTTTTTTAGTAAAACTCCTCATCTAAGAGAAGAG
AGAGAAACAAATACTTGATCTGAGTCCGGAGATTCTATTTGTCTCCAACAGTTTCC
TCTTGGTTTCTTGCATTCGCTGCAGCAAAACGCATCAAGAATTTAACCAACCAGCGA
AACACATATCAAGAAGAAGAAGAAAGATCTAAGAAGGAAAAAAACCTCATATTGA
GTGGCCCAAACATCGACATCAGAAATAGTTTGGTACAGATCTACGATCTCCTTCGTT
CTATAACCAACAAAATCACCAAAAAAGTAGTGGTTAATTATAAGAAAACAAAGCAA
CTCAATTAGCTTAATTTAAGAGTGGTGTTTAGAGAGATGGTGTACGTGGTGTTAGGG
CTGATATACTCATGAAGCTTGTTGGAGCTAGAGAACATGATAATCGAAACCCAGCA
TCACACAAAACCGTGAGCTCATGTGCTTTCTTGAATAAACCATTTCTTCTCTTTGAAT
ACGTCACTTGTCTGTTTGTCTGGTTCTCTATCCTCTTGATCTGGATCTTCCCTCTCGCC
ATATTCTTCTCTCTTTGTTTAATCTTTTTGTTGAAGAGATTTGGTGGAGAGGACAAGA
GATATAATGAGAAGAAAGAAGTGAAATAGAAAGAGAGAGATGGAGTTGAAGAAGT
AAAGGGTCCACTTGAGTTACTAAAAATGGAAAGTATTGCCTAATCCATGAAAGGTA
AGTTCAGAAGTTGATGAAAACTAAGTGATAAATTTTCCATTTATGTAAACTGATTTT
TTTAATTACAAGACACTGTTTAAATCAACGGACATCGATGGTTGTATAATTACAAGA
CACTGCTTAAATCAATTGTCACTTGGTAAAAGAGGGGGACCAAAGCTAAAAACTTG
GTTTGCTTTTCGTCAATTTATTAACGGAGCTCCGTTAGCTTCTACTTTGTTTTTGTTTA
GACGGTGACAAACTTAACGGCGTTTGTAAACGTCAAATCAGTGCAGGTGGATTTGGT
TGGCTTTTTACACTTACCCTAAAGTAAACAAAAGTGTTTAGGTGTGAACAAGTTTTT
ATATTGGTGTTAAAAGCCAATATTCTACTTTGTCTGTTAATTTGGGAAATAAGAAG
AAAGAGATATATATGTTTGGATTAATCGTCACTTCCATCTAACTCAAATCTTTTATAT
GTTTCCCCAAATGATTACAATAATTTCCCGGATTTGCCTTTAACTAAAGATCCTTGGA
AAATAGAATATTACCCCTAGGGTTTAAGAAGGAATCACAAGTTAGGAGAAAAGTCT
TTGTTTGTAGATAATGTTTGGTCCTAACTCCAAACAGTCCATCAAATCAGATATATG
ATGAAACTCTTTTTTCTTTTTGCTTCGACCAGTTAGTGTTGTTTCAAAACTAAGTTGG
CCACAGTTACTGTTGTTTTGAAA
```

LIPID METABOLISM REGULATORS IN PLANTS

CROSS REFERENCE TO RELATED APPLICATIONS

This application claims the priority benefit of U.S. Provisional Application Ser. No. 60/274,170 filed on Mar. 8, 2001.

FIELD OF THE INVENTION

The present invention relates in general to metabolism of seed storage compounds in plants. More specifically, the present invention relates to nucleic acid sequences encoding lipid metabolism regulator proteins and the use of these sequences in producing transgenic plants.

BACKGROUND OF THE INVENTION

The study and genetic manipulation of plants has a long history that began even before the famed studies of Gregor Mendel in the 19$^{th}$ century. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164) and rapeseed (Toepfer et al. 1995, Science 268:681-686), as well as non-traditional oil seed plants such as tobacco (Cahoon et al. 1992, Proc. Natl. Acad. Sci. USA 89:11184-11188).

Plant seed oils comprise both neutral and polar lipids (see Table 1). The neutral seed lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand a large number of unusual fatty acids can be incorporated into the neutral storage lipids in seeds of many plant species (Van de Loo, F. J. et al. 1993, Unusual Fatty Acids in Lipid Metabolism in Plants pp 91-126 editor T S Moore Jr. CRC Press).

Lipids are synthesized from fatty acids and their synthesis may be divided into two parts: the prokaryotic and the eukaryotic pathway (J Ohlrogge & J Browse 1995, Lipid Biosynthesis Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-ACP by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-keto-butyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Shanklin and Cahoon 1998, Annu. Rev. Plant Physiol. Plant Mol. Biol. 49:611-641; Voelker 1996, Genetic Engineering ed.: J K Setlow 18:111-13; Frentzen 1998, Lipid 100(4-5):161-166).

Acetyl-CoA in the plastids is the central precursor for lipid biosynthesis. Acetyl-CoA can be formed in the plastids by different reactions and the exact contribution of each reaction is still being debated (J Ohlrogge & J Browse 1995, Lipid Biosynthesis Plant Cell 7:957-970). It is however accepted that a large part of the acetyl-CoA is derived from glucose-6-phospate and pyruvate (i.d. phosphoenolpyruvate) that are imported from the cytoplasm into the plastids. Sucrose is produced in the source organs (leaves, where photosynthesis takes place) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone. For example, introduction of a $\Delta^{12}$-hydroxylase nucleic acid sequence into transgenic tobacco resulted in the introduction of a novel fatty acid, ricinoleic acid, into the tobacco seed oil (Van de Loo, et al. 1995, Proc. Natl. Acad. Sci USA 92:6743-6747). Tobacco plants have also been engineered to produce low levels of petroselinic acid by the introduction and expression of an acyl-ACP desaturase from coriander (Cahoon et al. 1992, Proc. Natl. Acad. Sci USA 89:11184-11188).

The modification of seed oil content in plants has significant medical, nutritional and economic ramifications. With regard to the medical ramifications, the long chain fatty acids (C18 and larger) found in many seed oils have been linked to reductions in hypercholesterolemia and other clinical disorders related to coronary heart disease (Brenner R. R. 1976, Adv. Exp. Med. Biol. 83:85-101). Therefore, consumption of a plant having increased levels of these types of fatty acids could reduce the risk of heart disease. Enhanced levels of seed oil content also increase large-scale production and thereby reduce the cost of these oils.

In order to increase or alter the levels of compounds such as seed oil in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as Brassica, soybean, carrot, pine and *Arabidopsis* have also been cloned and determined to encode proteins associated with the phospholipid monolayer membrane of oil bodies in those plants.

Although several nucleic acids that are involved in enzymatic steps of the metabolism of lipids, fatty acids and starches have been cloned and identified, there are likely a multitude of such plant nucleic acids that have yet to be identified. Phenotypic analysis of several oilseed plants and other mutated plants has revealed other putative proteins involved in plant lipid metabolism, but the prior art has yet to describe the genomic location of these proteins or the nucleic acids that encode them.

An exemplary study is that of the oilseed plant *Arabidopsis thaliana*. In 1998, Focks and Benning isolated and characterized a wrinkled mutant of *Arabidopsis thaliana* designated wri1 (Plant Physiology 1998, 118:91-101). The wri1 mutant has a decreased seed oil content that was speculated to be due to a defect in the seed-specific regulation of carbohydrate metabolism. In the wri1 mutant, the activities of several glycolytic enzymes were reduced and the mutant seeds were impaired in the incorporation of sucrose and glucose into triacylglycerol lipids, while important precursor molecules for plastidial lipid biosynthesis, like pyruvate and acetate, were incorporated at increased rates. This biochemical evidence was interpreted by Focks and Benning as indication that the WRI1 protein could be a regulatory protein governing carbohydrate metabolism during seed development or a hexokinase that may act as a sugar sensor in developing seeds, and thus controlling the activities of several glycolytic enzymes (Plant Physiology 1998, 118:91-101). The wri1 phenotype (wrinkled seeds) has been found in two different allelic *Arabidopsis thaliana* mutants, namely wri1-1 and wri1-2.

Since the discovery of the wri1 phenotype by Focks and Benning, the *Arabidopsis thaliana* genome was sequenced in its entirety (The *Arabidopsis Genome Initiative* 2000 Analysis of the genome sequence of the flowering plant *Arabidopsis thaliana*. Nature 408:796-844). These genomic sequences have been annotated and open reading frames encoding putative proteins have been assigned in an automatic process. Importantly however, this annotation is only based upon homologies with other sequences with known functions, and therefore, in no way identifies the true location, sequence or functionality of an *Arabidopsis thaliana* nucleic acid sequence. The annotation and assignment of open reading frames also in no way describes the location, function or sequence of the wri1 gene.

Therefore, what is needed in the art is the elucidation of the location and identity of the one or more nucleic acids associated with the wri1 mutation in *Arabidopsis thaliana* along with an understanding of the functionality of the proteins and protein fragments encoded by those nucleic acids.

BRIEF DESCRIPTION OF THE DRAWINGS

FIG. 3 is an alignment of the amino acid sequence of an ORF encoded by a WRI1 cDNA (SEQ ID NO:3) and the amino acid sequences of two separate ORFs (SEQ ID NO:8 and SEQ ID NO:9) that were predicted by automatic gene-finding programs. The alignment shows that WRI1 contains both of the predicted ORFs and in addition several amino acids, which are the results of differences in predicted splicing sites.

FIGS. 4(A-C) show the cDNA polynucleotide sequence (SEQ ID NO:1), open reading frame nucleotide sequence (SEQ ID NO:2) and amino acid sequence (SEQ ID NO:3) of a LMR from *Arabidopsis thaliana*.

FIGS. 5(A-C) show the cDNA polynucleotide sequence (SEQ ID NO:4), open reading frame nucleotide sequence (SEQ ID NO:5) and amino acid sequence of a LMR from *Arabidopsis thaliana*.

FIG. 6 shows the truncated polynucleotide sequence of BAC clone T12E18 (Genbank accession AL132971).

SUMMARY OF THE INVENTION

Figure 2:
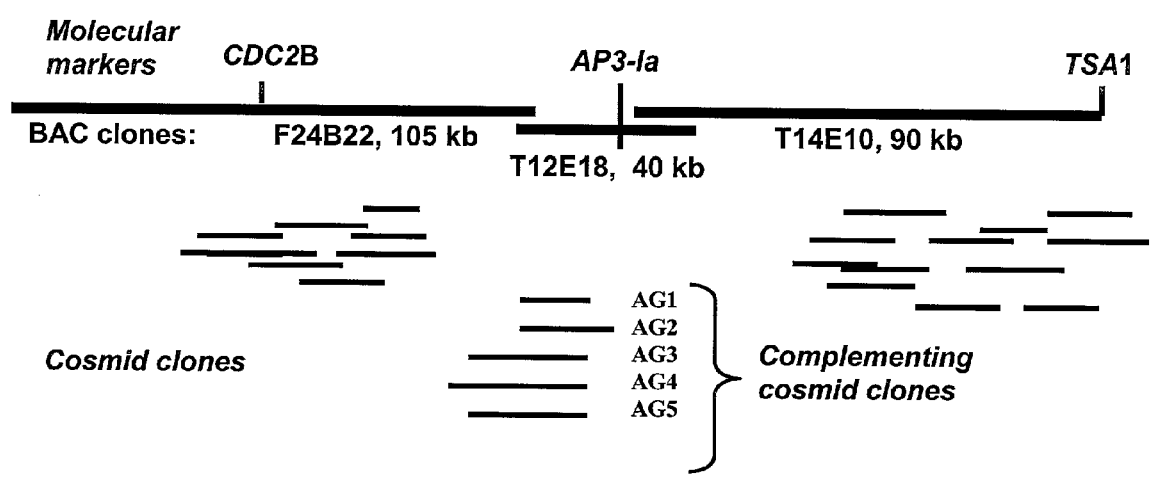
FIG. 2 is a schematic representation of the wri1 complementation strategy by using wild-type cosmid clones. The cosmids designated as AG1-3 and 5 did rescue the wri1 phenotype and restore seed oil content to near wild-type levels (cosmid AG4 was never successfully transformed). The region of overlap between the rescuing cosmids is 8.5 kb, indicating that the WRINKLED1 gene is contained within that 8.5 kb region.

The present invention is directed to novel isolated nucleic acid and amino acid sequences associated with the metabolism of seed storage compounds in plants. A novel discovery described herein lies in the identification of the nucleic acid sequences that encode the WRINKLED1 genetic locus (WRI1), and that thereby encode a Lipid Metabolism Regulator (LMR) genetic locus. The mutant wri1 nucleic acid sequence was first mapped to a one hundred and fifty kilobase interval lying between the markers CDC2BG and TSA1 on chromosome III of *Arabidopsis thaliana*. Transformation of the wri1 Arabidopsis mutant with cosmid binary vectors containing genomic sequences spanning this region lead to the discovery of four overlapping cosmids that complemented the wri1 mutant and restored the wild-type seed phenotype and seed oil content (FIG. 2 and Example 13). The smallest common genomic fragment on the five complementing cosmid binary vectors is 8.5 kb, indicating that the WRI1 gene is contained within that 8.5 kb region.

According to the automatically generated annotation of the genomic sequence in GenBank, this 8.5 kb fragment fully contains two open reading frames (ORFs, SEQ ID NOs:8 and 9) and the partial fragments of another two ORFs. However, by using RT-PCR and RACE-PCR it was determined that the two ORFs (SEQ ID NOs:8 and 9) are actually part of the same gene containing an unusually long intron of 1641 nucleotides. Based on the wri1 mutant and the mapping data this gene was named "WRI1". The full-length WRI1 cDNA was isolated by RT-PCR using a proof-reading polymerase and its nucleotide sequence was determined (SEQ ID NO:1). The cDNA encoded by this gene is 1539 bp long, a 166 bp 3' UTL and contains a 1293 bp ORF (SEQ ID NO:2) encoding a protein of 430 amino acids (SEQ ID NO:3). The WRI1 cDNA shows small sequence homologies with a known transcription factor, Aintegumenta, and contains an Apetala-2-like DNA binding domain. The AP2-like domains span amino acids 64-134 and 166-225 of SEQ ID NO:3. Other interesting repeats in SEQ ID NO:3 span amino acids 11-21, 266-272 and 401-423. Alternate sequence for the full-length WRI1 cDNA, ORF and encoded protein are shown in SEQ ID NO:4, SEQ ID NO:5 and SEQ ID NO:6, respectively. It is therefore proposed that WRI1 acts as a transcription factor regulating lipid and seed storage compound metabolism during seed development. These newly discovered nucleic acid and amino acid sequences have been labeled herein as Lipid Metabolism Regulator (or LMR) nucleic acid and amino acid sequences.

Accordingly, the present invention relates to the use of LMR nucleic acids in the production of transgenic plants having a modified level of a seed storage compound. A method of producing a transgenic plant with a modified level of a seed storage compound includes the steps of transforming a plant cell with an expression vector comprising a LMR nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, pepper, tagetes, cotton, oil palm, coconut palm, flax, castor and peanut, for example.

Also included herein is a seed produced by a transgenic plant transformed by a LMR polynuclteotide sequence, wherein the seed contains the LMR polynuclteotide sequence and wherein the plant is true breeding for a modified level of a seed storage compound. The present invention additionally includes a seed oil produced by the aforementioned seed.

According to the present invention, the compositions and methods described herein can be used to increase or decrease the level of a lipid in a seed oil, or to increase or decrease the level of a fatty acid in a seed oil, or to increase or decrease the level of a starch in a seed or plant. A method of producing a higher-than-normal level of storage compound in a transgenic plant, comprises expressing a LMR nucleic acid from *Arabidopsis thaliana* in the transgenic plant, wherein the transgenic plant is a species different from *Arabidopsis thaliana*. Also included herein are compositions and methods for the modification of the efficiency of production of a seed storage compound.

Accordingly, it is an object of the present invention to provide novel isolated LMR nucleic acids and isolated LMR amino acid sequences from *Arabidopsis thaliana*, as well as active fragments, analogs and orthologs thereof.

It is another object of the present invention to provide transgenic plants having modified levels of seed storage compounds, and in particular, modified levels of a lipid, a fatty acid or a starch.

It is a further object of the present invention to provide methods for producing such aforementioned transgenic plants.

It is another object of the present invention to provide seeds and seed oils from such aforementioned transgenic plants.

These and other objects, features and advantages of the present invention will become apparent after a review of the following detailed description of the disclosed embodiments and the appended claims.

DETAILED DESCRIPTION

The present invention is directed to a transgenic plant with a modified level of a seed storage compound and a method for producing the same. The present invention also encompasses a seed produced by a transgenic plant with a modified level of a seed storage compound and a method for producing the same. Preferably, the plant is of an oil producing species and the seed storage compound is a fatty acid, lipid or starch.

The present invention additionally includes one or more nucleic acid sequences that encode and direct the expression of proteins that regulate the metabolism of a seed storage compound. These nucleic acid sequences are termed "lipid metabolism regulator" nucleic acid sequences and are referred to hereinafter as "LMR nucleic acids" or "LMR polynucleotides." It is to be understood however that the nomenclature used herein in no way limits the functionality of the amino acid sequences encoded by the nucleic acid sequences described herein. In one embodiment, a LMR nucleic acid described herein is introduced into a plant, preferably of oil producing species, resulting in the modification of the levels of a seed storage compound therein. As used herein, the terms "a" or "an" can mean more than one, depending upon the context in which it is used.

"Plants" refer to photosynthetic organisms, both eukaryotic and prokaryotic, whereas the term "higher plants" refers to eukaryotic plants. "Oil producing species" as used herein refers to plant species that produce and store triacylglycerol in specific organs and primarily in seeds. Plants of oil producing species include, but are not limited to, rapeseed, canola, linseed, soybean, sunflower, maize, oat, rye, barley, wheat, pepper, tagetes, cotton, oil palm, coconut palm, flax, castor and peanut. The group of plants of oil producing species also includes non-agronomic species that are useful in developing appropriate expression vectors such as tobacco, rapid cycling Brassica species, *Arabidopsis thaliana* and wild species that may be a source of unique fatty acids. In addition to plants of oil producing species, tuberous plants are also included in the present invention.

As used herein, the term "seed storage compound" refers to a lipid, a fatty acid, a starch or a seed storage protein. The term "lipid" includes, but is not limited to, a triacylglycerol lipid, a plastidial lipid, or a membrane lipid. Lipids classes included in the present invention are shown in Table 1 below. In one embodiment of the present invention, a LMR nucleic acid of the present invention regulates the metabolism of a triacylglycerol lipid, a membrane lipid, or both. The term "fatty acid" is well known to one of ordinary skill in the art and includes both saturated fatty acids and polyunsaturated fatty acids, including, but not limited to, those fatty acids listed in Table 2 below. The term "starch" is well known to one of ordinary skill in the art and as used herein includes amylose and amylopectin. The term "seed storage protein" is well known to one of ordinary skill in the art and includes 2S albumin protein, cruciferin protein, 12S albumin protein and oleosin.

TABLE 1

Plant Lipid Classes

| Neutral Lipids | Triacylglycerol (TAG) |
| --- | --- |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

Common Plant Fatty Acids

| 16:0 | Palmitic acid |
| --- | --- |
| 16:1 | Palmitoleic acid |
| 16:3 | Palmitolenic acid |

TABLE 2-continued

Common Plant Fatty Acids

| 18:0 | Stearic acid |
|---|---|
| 18:1 | Oleic acid |
| 18:2 | Linoleic acid |
| 18:3 | Linolenic acid |
| g-18:3 | Gamma-linolenic acid * |
| 20:0 | Arachidic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

* These fatty acids do not normally occur in plant seed oils, but their production in transgenic plant seed oil is of importance in plant biotechnology.

Figure 1:
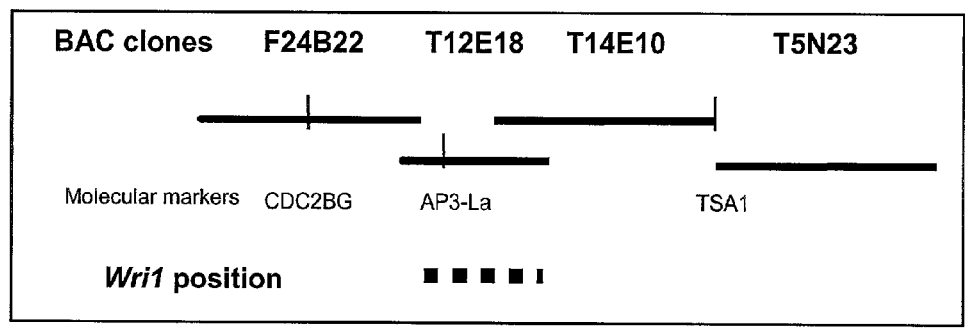
FIG. 1 is a schematic representation of the position of the BAC clones, F24B22, T12E18, T14E10 and T5N23, the markers therein and the LMR genetic locus (denoted as "WRI1 position").

The ability to produce a transgenic plant having a modified level of a seed storage compound lies in a novel discovery described herein comprising the identification of the nucleic acid sequences that encode the WRI1 genetic locus, and that thereby encode a lipid metabolism regulator (LMR) genetic locus. More particularly, the present invention provides LMR polynucleotide and polypeptide sequences located within the LMR genetic locus. In order to identify the LMR polynucleotide and polypeptide sequences, the mutant wri1 nucleic acid sequence was first mapped to a one hundred and fifty five kilobase interval lying between the markers CDC2BG and TSA1 on chromosome III (see Table 3 and FIG. 1). Therefore, the term "LMR genetic locus" refers to a nucleic acid sequence between the markers CDC2BG and TSA1 on chromosome III of *Arabidopsis thaliana*. As shown in FIG. 1, the CDC2BG marker is located on the F24B22 BAC clone (Genbank accession number AL132957) while the TSA1 marker is located on both the 5' end of the T14E10 BAC clone (Genbank accession number AL138656) and on the 3' end of the T5N23 BAC clone (Genbank accession number AL132970). Portions of the LMR genetic locus are therefore located on the two BAC clones, F24B22 and T14E10 as well as an intervening BAC clone, T12E18 (Genbank accession number 132971).

Anyone of ordinary skill in the art will recognize that the discovery of the exact location of a genetic lesion like wri1 on a chromosome is a significant and useful advance in the identification of the nucleic acid sequence and its encoded protein that is responsible for the WRI1 phenotype. Similarly, anyone of ordinary skill in the art will recognize that the mapping of a mutation to certain nucleic acid sequences with hitherto unknown function at that location on the chromosome, gives unequivocal evidence of the function of the nucleic acids at that locus and their encoded proteins.

Accordingly, in a preferred embodiment of the present invention, an isolated LMR amino acid sequence participates in the metabolism of compounds necessary for the construction of cellular membranes, seed storage lipids and fatty acids, or starch or seed proteins in a plant cell, preferably located in seeds, or in the transport of molecules across its membranes. In a further preferred embodiment, the LMR nucleic acid encoding the LMR amino acid sequence is located on chromosome III of *Arabidopsis thaliana*. In a still further preferred embodiment, the LMR nucleic acid is located on the LMR genetic locus as described herein. Particularly, the LMR nucleic acid is located between the markers CDC2BG and TSA1 on chromosome III of *Arabidopsis thaliana*. In one embodiment of the present invention, the LMR nucleic acid comprises a polynucleotide sequence selected from the group consisting of a polynucleotide of SEQ ID NO:1; a polynucleotide of SEQ ID NO:2; a polynucleotide of SEQ ID NO:4; a polynucleotide of SEQ ID NO:5; a polynucleotide sequence encoding a polypeptide of SEQ ID NO:3; a polynucleotide sequence encoding a polypeptide of SEQ ID NO:6, a polynucleotide comprising at least 60 consecutive nucleotides of any of the aforementioned polynucleotides; a polynucleotide having at least 70% sequence identity with any of the aforementioned polynucleotides; a polynucleotide encoding a polypeptide having at least 70% sequence identity with any of the aforementioned polypeptides; and a polynucleotide complementary to any of the aforementioned polynucleotides. In a further preferred embodiment, the LMR nucleic acid comprises a polynucleotide sequence shown in SEQ ID NO:1, SEQ ID NO:2, SEQ ID NO:4 or SEQ ID NO:5.

As used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The invention further provides an isolated LMR coding nucleic acid. In preferred embodiments, the LMR coding nucleic acid is selected from a polynucleotide shown in SEQ ID NO:2 and a polynucleotide shown in SEQ ID NO:5.

Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e., sequences located at the 5' and 3' ends of the nucleic acid) in its naturally occurring replicon. For example, a cloned nucleic acid is considered isolated. In various embodiments, the isolated LMR nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an *Arabidopsis thaliana* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized. In one embodiment, the language "substantially free of other cellular material" includes preparations of LMR amino acid sequences having less than about 30% (by dry weight) of non-LMR amino acid sequence (also referred to herein as "contaminating protein"), more preferably less than about 20% contaminating protein, still more preferably less than about 10% of contaminating protein, and most preferably less than about 5% of contaminating protein.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

The LMR nucleic acids of the present invention are preferably produced by recombinant DNA techniques. For example, a LMR nucleic acid molecule encoding a LMR polypeptide is cloned into an expression vector, the expression vector is introduced into a host cell, and the LMR nucleic acid is expressed in the host cell. The LMR protein can then be isolated from the cells by an appropriate purification scheme using standard polypeptide purification techniques. For the purposes of the invention, the term "recombinant polynucleotide" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a LMR protein or peptide can be synthesized chemically using standard peptide synthesis techniques. Moreover, a native LMR protein can be isolated from cells (e.g., *Arabidopsis thaliana*), for example using an anti-LMR protein antibody, which can be produced by standard techniques utilizing a LMR protein or fragment thereof.

As used herein, the terms "polypeptide" and "protein" refer to a chain of at least four amino acids joined by peptide bonds. The chain may be linear, branched, circular or combinations thereof. In a preferred embodiment, the LMR protein is an *Arabidopsis thaliana* protein that regulates the metabolism of a seed storage compound in a plant. In a further preferred embodiment, the LMR protein comprises a polypeptide sequence as shown in SEQ ID NO:3 or SEQ ID NO:6. It is also to be understood that the LMR polypeptides of the present invention include those encoded by a polynucleotide sequence shown in SEQ ID NO:2 or SEQ ID NO:5 with or without post-translational modifications. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In one embodiment of the present invention, the LMR polynucleotides and polypeptides are derived from an *Arabidopsis* species, and more preferably, *Arabidopsis thaliana*.

In addition to the LMR polynucleotide and polypeptide sequences described above, the present invention includes LMR polynucleotide and polypeptide fragments and plants and plant cells containing these fragments. A LMR polynucleotide fragment can comprise a portion of the sequence in SEQ ID NO:1, SEQ ID NO:2, SEQ ID NO:4 or SEQ ID NO:5, for example, a fragment that can be used as a probe or primer. As used herein, the term "fragment" means at least 20 contiguous amino acids, preferably at least 30 contiguous amino acids, more preferably at least 50 contiguous amino acids, and most preferably at least 60 to 80 or more contiguous amino acids. Fragments of LMR proteins can be generated by methods known to those skilled in the art or may result from normal protein processing (e.g. removal of amino acids from the nascent polypeptide that are not required for biological activity or removal of amino acids by alternative mRNA splicing or alternative protein processing events). In a preferred embodiment, a LMR protein fragment retains the biological activity of the full-length LMR protein. As used herein, the term "biologically active portion of" a LMR polypeptide is intended to include a portion, e.g., a domain/motif, of a LMR polypeptide that participates in the modulation of seed storage compound levels in a plant.

The invention also provides LMR chimeric or fusion polypeptides that can be used to transform a plant and modulate seed storage compounds in the plant. As used herein, an LMR "chimeric polypeptide" or "fusion polypeptide" comprises an LMR polypeptide operatively linked to a non-LMR polypeptide. A non-LMR polypeptide has both a different polypeptide sequence and has a different function than a LMR polypeptide. Within the fusion polynucleotide, the term "operably linked" is intended to indicate that the LMR polypeptide and the non-LMR polypeptide are fused to each other so that both sequences fulfill the proposed function attributed to the sequence used. The non-LMR polypeptide can be fused to the N-terminus or C-terminus of the LMR polypeptide. One example of non-LMR polypeptide is a heterologous signal sequence.

In one embodiment of the present invention, a LMR nucleic acid described herein is operably linked to a non-LMR nucleic acid or a heterologous nucleic acid sequence, both hereinafter referred to as a "chimeric LMR nucleic acid." In preferred embodiments, the chimeric LMR protein encoded by the chimeric LMR nucleic acid has an activity that differs from that of the LMR protein alone. The heterologous nucleic acid sequence can be a nucleic acid sequence from any plant other than *Arabidopsis thaliana*, however, it is preferred that the chimeric LMR protein participates in the metabolism of compounds necessary for the synthesis of lipids, fatty acids or starch in plants, or in the transport of molecules across the membranes of plants. In particularly preferred embodiments, integration of the chimeric LMR nucleic acid into a host cell modulates production of a desired seed storage compound by the cell. Examples of heterologous nucleic acid sequences useful for practicing the present invention include storage proteins, co-factors and enzymes involved in the metabolism of seed storage compounds including lipid desaturases such as $\Delta^6$-desaturases, $\Delta^{12}$-desaturases, $\Delta^4$- desaturases and other related desaturases such as stearoyl-ACP desaturases, acyl carrier proteins, thioesterases, acetyl transacylases, acetyl-coA carboxylases, ketoacyl-synthases, malonyl transacylases and elongases.

Standard techniques for construction of such chimeric LMR nucleic acids are well known to those of ordinary skill in the art and can be found in references such as Sambrook et al., Molecular Cloning: A Laboratory Manual. $2^{nd}$ ed., Cold Spring Harbor Laboratory, Cold Spring Harbor Laboratory Press, Cold Spring Harbor, N.Y., 1989 (or latest edition). A variety of strategies are available for ligating fragments of DNA, the use of which depends on the nature of the termini of the DNA fragments. One of ordinary skill in the art recognizes that in order for the heterologous nucleic acid sequence to be expressed, the construction of the expression vector requires promoter elements and signals for efficient polyadenylation of the transcript. Accordingly, the LMR regulatory region that contains the consensus promoter sequence known as the TATA box can be ligated directly to a promoterless heterologous coding sequence. Additionally, the 3' end of a heterologous nucleic acid sequence can be ligated to a termination sequence comprising a polyadenylation site or the polyadenylation site can be provided by the heterologous nucleic acid sequence itself.

Also included herein are LMR nucleic acids attached to a moiety. These moieties include, but are not limited to, detection moieties, hybridization moieties, purification moieties, delivery moieties, reaction moieties, binding moieties, and the like. When a LMR nucleic acid is used as a probe, the detection moiety attached to the nucleic acid can be selected from a radioisotope, a fluorescent compound, an enzyme or an enzyme co-factor.

In addition to LMR fragments and LMR chimeric or fusion polypeptides, the present invention includes a homolog, an allelic variant, an analog, an ortholog, or a paralog of a naturally occurring LMR protein in a plant of oil producing species. Whereas the differences in amino acid sequences between a naturally occurring LMR protein and its allelic variant are natural, the differences in amino acid sequences between a naturally occurring LMR protein and its analog, ortholog or paralog can be natural or induced. As used herein a "naturally occurring protein" refers to an amino acid sequence that occurs in nature. Preferably, a naturally occurring LMR protein comprises an amino acid sequence corresponding to SEQ ID NO:3 or SEQ ID NO:6.

One susbset of LMR homologs is allelic variants. As used herein, the term "allelic variant" refers to a nucleic acid sequence that occurs at a LMR genetic locus in an *Arabidopsis thaliana* plant. Such natural allelic variations can typically result in 1-5% variance in a LMR nucleic acid. At least two allelic variants of a LMR nucleic acid have been identified phenotypically and labeled wri1-1 and wri1-2. Alternative alleles can be identified by sequencing the nucleic acid sequence of interest in a number of different plants, which can be readily carried out by using hybridization probes to identify the same LMR genetic locus in those plants. Any and all such nucleic acid variations and resulting amino acid polymorphisms or variations in a LMR protein that are the result of natural allelic variation and that do not alter the functional activity of a LMR protein are intended to be within the scope of the invention.

Moreover, nucleic acid molecules encoding LMR analogs, orthologs and paralogs, which have a polynucleotide sequence that differs from that of an *Arabidopsis thaliana* LMR gene, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Normally, paralogs have different functions, but these functions may be related (Tatusov, R. L. et al. 1997, Science 278(5338):631-637). Orthologs of the invention will generally exhibit at least 80-85%, more preferably 90%, and most preferably 95%, 96%, 97%, 98% or even 99% identity or homology with all or part of a naturally occurring LMR amino acid sequence. The length of sequence comparison is at least 15 amino acid residues, preferably at least 25 amino acid residues, and more preferably at least 35 amino acid residues.

To determine the percent sequence identity of two amino acid sequences (e.g., the sequences of SEQ ID NO:3 or SEQ ID NO:6, and a mutant or homolog thereof), the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence (e.g., SEQ ID NO:3 or SEQ ID NO:6) is occupied by the same amino acid residue as the corresponding position in the other sequence (e.g., a mutant or homolog of the sequence shown in SEQ ID NO:3 or SEQ ID NO:6), then the molecules are identical at that position. The same type of comparison can be made between two nucleic acid sequences.

Accordingly, the percent sequence identity between the two sequences is a function of the number of identical positions shared by the sequences (i.e., percent sequence identity=numbers of identical positions/total numbers of positions×100). For the purposes of the invention, the percent sequence identity between two polynucleotide or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two polynucleotides. A gap opening penalty of 10 and a gap extension penalty of 0.1 are used for determining the percent identity of two polypeptides. All other parameters are set at the default settings. It is to be understood that for the purposes of determining sequence identity when comparing a DNA sequence to an RNA sequence, a thymidine nucleotide is equivalent to a uracil nucleotide.

Preferably, the isolated amino acid homologs included in the present invention are at least about 50-60%, preferably at least about 60-70%, more preferably at least about 70-75%, 75-80%, 80-85%, 85-90% or 90-95%, and most preferably at least about 96%, 97%, 98%, 99% or more identical to an entire amino acid sequence shown in SEQ ID NO:3 or SEQ ID NO:6. In yet another embodiment, the isolated amino acid homologs included in the present invention are at least about 50-60%, preferably at least about 60-70%, more preferably at least about 70-75%, 75-80%, 80-85%, 85-90% or 90-95%, and most preferably at least about 96%, 97%, 98%, 99% or more identical to an entire amino acid sequence encoded by a nucleic acid sequence shown in SEQ ID NO:2 or SEQ ID NO:5. In other embodiments, the LMR amino acid homologs have sequence identity over at least 15 contiguous amino acid residues, more preferably at least 25 contiguous amino acid residues, and most preferably at least 35 contiguous amino acid residues of SEQ ID NO:3 or SEQ ID NO:6. It is further preferred that the LMR amino acid homolog function to modulate a seed storage compound in a plant.

In another preferred embodiment, a LMR polynucleotide homolog of the invention comprises a nucleotide sequence which is at least about 50-60%, preferably at least about 60-70%, more preferably at least about 70-75%, 75-80%, 80-85%, 85-90% or 90-95%, and even more preferably at least about 95%, 96%, 97%, 98%, 99% or more identical to a nucleotide sequence shown in SEQ ID NO:1, SEQ ID NO:2, SEQ ID NO:4 or SEQ ID NO:5, or to a portion comprising at least 60 consecutive nucleotides thereof. The preferable length of sequence comparison for nucleic acids is at least 75 nucleotides, more preferably at least 100 nucleotides and most preferably the entire length of the coding region. It is further preferred that the LMR polynucleotide homolog modulate a seed storage compound in a plant, for example, the level of a seed storage compound when expressed or over-expressed therein.

Nucleic acid molecules corresponding to natural allelic variants and analogs, orthologs and paralogs of a LMR cDNA can be isolated based on their identity to the *Arabidopsis thaliana* LMR nucleic acids described herein using LMR cDNAs, or a portion thereof, as a hybridization probe according to standard hybridization techniques under stringent hybridization conditions. Therefore, the present invention includes a nucleic acid sequence that hybridizes (under stringent or highly stringent conditions) to a nucleic acid sequence shown in SEQ ID NO:1, SEQ ID NO:2, SEQ ID NO:4 or SEQ ID NO:5.

As used herein with regard to hybridization for DNA to DNA blot, the term "stringent conditions" refers to hybridization overnight at 60° C. in 10× Denhart's solution, 6× SSC, 0.5% SDS and 100 µg/ml denatured salmon sperm DNA. Blots are washed sequentially at 62° C. for 30 minutes each time in 3× SSC/0.1% SDS, followed by 1× SSC/0.1% SDS and finally 0.1× SSC/0.1% SDS. As also used herein, "highly stringent conditions" refers to hybridization overnight at 65° C. in 10× Denhart's solution, 6× SSC, 0.5% SDS and 100 µg/m 1 denatured salmon sperm DNA. Blots are washed sequentially at 65° C. for 30 minutes each time in 3× SSC/0.1% SDS, followed by 1× SSC/0.1% SDS and finally 0.1× SSC/0.1% SDS. Methods for nucleic acid hybridizations are described in Meinkoth and Wahl, 1984 Anal. Biochem. 138:267-284; Current Protocols in Molecular Biology, Chapter 2, Ausubel et al. Eds., Greene Publishing and Wiley-Interscience, New York, 1995; and Tijssen, Laboratory Techniques in Biochemistry and Molecular Biology: Hybridization with Nucleic Acid Probes, Part I, Chapter 2, Elsevier, N.Y., 1993. Preferably, an isolated nucleic acid molecule of the invention that hybridizes under stringent or highly stringent conditions to a sequence of SEQ ID NO:1, SEQ ID NO:2, SEQ ID NO:4 or SEQ ID NO:5 corresponds to a naturally occurring nucleic acid molecule.

The skilled artisan will appreciate that changes can be introduced by mutation into the amino acid sequence of a LMR protein without affecting the biological activity of the LMR protein. Mutations can be introduced by standard techniques, such as site-directed mutagenesis and PCR-mediated mutagenesis. Amino acid residues that are not conserved or only semi-conserved among LMR proteins of various species may be non-essential for activity and thus would likely be targets for alteration. A "non-essential" amino acid is a residue that can be altered from the wild-type sequence of a LMR protein (i.e., SEQ ID NO:3 or SEQ ID NO:6) without altering the biological activity, whereas an "essential" amino acid residue is required for biological activity. An "essential" amino acid includes a residue that can be altered from the wild-type sequence of a LMR protein (i.e., SEQ ID NO:3 or SEQ ID NO:6) to modify or abolish its biological activity without interfering in its binding with other proteins, ligands or binding sites.

In a preferred embodiment, an isolated LMR protein or portion thereof, while mutated from SEQ ID NO:3 or SEQ ID NO:6, is still sufficiently similar to an amino acid sequence corresponding to SEQ ID NO:3 or SEQ ID NO:6 such that the protein or portion thereof maintains the ability to participate in the metabolism of compounds necessary for the seed storage lipids, fatty acids and starch in plant seeds. Amino acids that are conserved among the LMR proteins of various species may be essential for activity and thus would not likely be targets for alteration, unless one wishes to increase, reduce or alter the activity of a LMR protein. Accordingly, one aspect of the invention pertains to nucleic acid molecules encoding LMR proteins that contain changes in amino acid residues that are not essential for activity. In one embodiment, the isolated nucleic acid molecule encodes a protein that includes an amino acid sequence that has at least about 45%, 65%, 75%, 85%, 95% or 98% identity with the amino acid sequence of SEQ ID NO:3 or SEQ ID NO:6, and which can participate in the metabolism of a seed storage compound.

In a preferred embodiment of the present invention, changes made at one or more predicted non-essential amino acid residues are conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagines, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted, nonessential amino acid residue in a LMR protein is preferably replaced with another amino acid residue from the same side chain family.

The skilled artisan will also appreciate that changes can be introduced by mutation into the amino acid sequence of a LMR protein that change or abolish the biological activity of the LMR protein without affecting its ability to interact with other proteins in the cell. This strategy is also known as "dominant negative mutation" in the art and provides an effective method for modulating the activity and function of regulatory and enzymatic proteins, whereby the activity of the functional endogenous protein is being titrated out by the non-functional form of the protein competing for interactions with other proteins, ligands or binding sites necessary for its function. Amino acid residues that are highly conserved or only semi-conserved among LMR proteins of various species may be "essential" for activity and thus would likely be targets for such alterations. In a preferred embodiment, an isolated LMR protein or portion thereof is sufficiently similar to an amino acid sequence corresponding to SEQ ID NO:3 or SEQ ID NO:6 such that the protein or portion thereof maintains the ability to participate in the metabolism of compounds necessary for the seed storage lipids, fatty acids and starch in plant seeds by competing with the amino acid sequence corresponding to SEQ ID NO:3 or SEQ ID NO:6 for interactions with other proteins, ligands or binding sites.

Two mutations that may or may not be dominant negative mutations, but that are included within the present invention, are those mutations found in the wri1-1 and wri1-2 plants. The wri1-1 plant contains a single mutation at nucleotide position 3197 on the T12E18 BAC sequence provided in SEQ ID NO:7 and shown in FIG. 6. This mutation is a G to A conversion in the intron splicing site that causes incomplete or altered splicing as compared to the wild-type wri1 nucleic acid sequence. A truncated and non-active form of the wri1 protein results from the wri1-1 mutation since the altered splicing causes the open reading frame to extend into the wild-type intron up to a stop codon. Accordingly, the present invention encompasses LMR polynucleotides containing a mutation at a site corresponding to nucleotide position 3197 on the T12E18 BAC sequence provided in SEQ ID NO:7.

There are a number of mechanisms by which the mutation of a LMR nucleic acid or protein of the invention may directly affect the yield, production, and/or efficiency of production of a seed storage compound from a plant of oil producing species. For example, a LMR protein involved in the transport of a seed storage compound in the cell may be increased in number or activity such that greater quantities of the seed storage compound precursors are imported from the cell exterior space and partitioned into the biosynthetic flux or deposited in the seed storage compounds. The yield, production and/or efficiency of production of a seed storage compound may also be increased when an increase in a LMR protein involved in the transport of that compound results in the allocation of the compound to a different plant cell compartment. Similarly, a LMR protein involved in the import of nutrients into cells or into cellular sub-compartments necessary for the biosynthesis of one or more seed storage compounds may be increased in number or activity such that these precursors, cofactors, or intermediate compounds are increased in concentration within the cell or the plastids or within the seed storage compartments. The seed storage compartments include, but are not limited to, oil bodies, microsomes, seed endosperm, amyloplasts and protein storage granules. Further, an increase in the yield, production and/or efficiency of production of a seed storage compound may be achieved by impairing the activity of one or more LMR proteins directly or indirectly involved in the degradation of seed storage compounds. The relative proportions of the various seed storage compounds (lipids, starch and proteins) can be altered so as to change or improve the extractions and processing of these compounds from seeds or so as to become more suitable for further uses (in for example animal feeds, human food or industrial purposes).

In some special cases, the altered expression of a LMR protein, or analog, ortholog or paralog thereof, or expression of an altered version of a LMR protein, or analog, ortholog or paralog thereof, can lead to the increased production of plant storage compounds in seeds of transgenic plants without manifesting itself in an increased yield (yield per hectar) of the wanted seed storage compound. This can be due to the increased degradation of the seed storage compound that can be either lipids, proteins or starch. It is possible to utilize the increased flux of intermediates through the degradative pathways for the production of other compounds of interest. For example, the increased flux of fatty acids to fatty acid beta-oxidation can be used to increase the production of polyhydroxyalkanoates in peroxisomes of transgenic plants.

Modification of the balance of lipids and/or fatty acids in a seed can have a profound effect on the lipid composition of the membrane of the seed cell. Since each type of lipid has different physical properties, an alteration in the lipid composition of a membrane can significantly alter membrane fluidity. Changes in membrane fluidity can impact the transport of molecules across the membrane, as well as the integrity of the cell, both of which have a profound effect on the production of "fine chemicals" from plants. These changes can also influence other characteristic like tolerance towards abiotic and biotic stress conditions.

The term "fine chemical" is art-recognized and includes molecules produced by an organism which have applications in various industries, such as, but not limited to, the pharmaceutical, agriculture, and cosmetics industries. Such compounds include lipids, fatty acids, cofactors and enzymes, both proteinogenic and non-proteinogenic amino acids, purine and pyrimidine bases, nucleosides, and nucleic acids (as described e.g. in Kuninaka, A. (1996) Nucleic acids and related compounds, p. 561-612, in Biotechnology vol. 6, Rehm et al., eds. VCH: Weinheim, and references contained therein), lipids, both saturated and polyunsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, Vitamins, pp. 443-613 (1996) VCH: Weinheim and references therein; and Ong, A. S., Niki, E. & Packer, L. (1995) Nutrition, Lipids, Health, and Disease, Proceedings of the UNESCO/Confederation of Scientific and Technological Associations in Malaysia, and the Society for Free Radical Research, Asia, held Sep. 1-3, 1994 at Penang, Malaysia, AOCS Press, (1995), enzymes, and all other chemicals described in Gutcho (1983) Chemicals by Fermentation, Noyes Data Corporation, and references therein.

In addition to the LMR nucleic acids described above, another aspect of the invention pertains to isolated nucleic acid sequences that are antisense thereto. An "antisense" nucleic acid sequence comprises a sequence that is complementary to a "sense" nucleic acid sequence encoding a protein, e.g., complementary to the coding strand of a double-stranded cDNA molecule or complementary to an mRNA sequence. The antisense nucleic acid can be complementary to an entire LMR nucleic acid or to only a portion thereof. In one embodiment, an antisense nucleic acid sequence is antisense to a "coding region" of the coding strand of a nucleic acid sequence encoding a LMR protein. The terms "coding region" and "non-coding region" are defined above. An antisense nucleic acid sequence can be constructed using chemical synthesis and enzymatic ligation reactions using procedures known to those of skill in the art. Antisense nucleic acids can be used in a method to downregulate the expression of endogenous LMR genes in order to manipulate seed storage compound metabolism. Antisense nucleic acid constructs generally lead to the formation of RNA secondary structures that are recognized and degraded by cellular RNAses and thereby lead to decreased mRNA abundance of the target gene, i.e. an endogenous gene. Accordingly, antisense nucleic acids that are complementary to the entire or to only a portion of the LMR nucleic acid sequence shown as SEQ NO:1, SEQ NO:2, SEQ NO:4 or SEQ ID NO:5 can be used to manipulate seed storage compound metabolism.

Another method to decrease the mRNA transcript levels of target genes is called 'RNA interference' or 'double-stranded RNA interference' (dsRNAi). Those skilled in the art are familiar with dsRNAi as an effective alternative to antisense techniques. In order to decrease the mRNA transcript levels of the target gene, i.e. an LMR nucleic acid, a construct is made that contains a portion of the LMR coding sequence in the sense and antisense orientation, where the sense and antisense sequences are separated by a linker region. The expression of such a dsRNAi construct in cells leads to the formation of stable double-stranded RNA secondary structures, which in turn leads to the recognition and destruction of the structures and the LMR transcripts through cellular mechanisms. Accordingly, nucleic acid sequences that are complementary to the entire or to only a portion of a LMR nucleic acid sequence provided under SEQ ID NO:1, SEQ ID NO:2, SEQ ID NO:4 or SEQ ID NO:5 can be used to manipulate seed storage compound metabolism by using RNA interference.

In addition to antisense LMR nucleic acids, also described herein are recombinant expression vectors and expression cassettes comprising the LMR nucleic acids described herein and host cells into which such vectors and cassettes have been introduced. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adenoassociated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., LMR proteins, mutant forms of LMR proteins, fusion polypeptides, etc.).

As used herein, the term "recombinant LMR protein" refers to a LMR protein expressed by a recombinant expression vector comprising a LMR nucleic acid. The host cell may be derived from bacteria, yeast or plant material. In one embodiment, the host cell is a capable of storing seed storage compounds. In a further embodiment, the host cell is capable of storing a seed storage compound in a way that facilitates harvesting of the desired compound from the cell. Preferably the host cell is a storage tissue cell such as an epidermal cell or a seed cell. The host cell as described above may be found or located in a plant tissue, a plant organ or a whole plant. It is to be understood that the term "host cell" refers not only to the particular subject cell, but also to the progeny or potential progeny of such a cell. Because certain modification may occur in succeeding generations due to either mutation or environmental influences, such progeny may not be identical to the parent cell, but are still included within the scope of the term as used herein.

Expression vectors suitable for use in plants, and therefore suitable for use in the present invention, are well known to those of skill in the art. Several examples of suitable expression vectors can be found in the following references: Plant Molecular Biology and Biotechnology, Chapter 6/7, S.71-119, CRC Press, Boca Raton, Fla., 1993; F. F. White, Vectors for Nucleic acid sequence Transfer in Higher Plants in Transgenic Plants, Vol. 1, Engineering and Utilization, p. 44-38, eds.: Kung und R. Wu, Academic Press, 1993; B. Jenes et al., Techniques for Nucleic acid sequence Transfer in Transgenic Plants, Vol. 1, Engineering and Utilization, p. 128-143, eds.: Kung und R. Wu, Academic Press, 1993; Potrykus, 1991, Annu. Rev. Plant Physiol. Plant Molec. Biol. 42:205-225.

The present invention additionally includes methods of expressing the LMR proteins described herein. As described in further detail below, a wild-type or mutant LMR nucleic acid is introduced into a host cell and either maintained on a separate plasmid or integrated into the genome of a host cell. The expressed LMR protein can be isolated from the medium in which the host cell is grown or from the host cell itself. Several non-limiting methods of expression and isolation of LMR proteins are described in the Examples below.

It is to be understood that the LMR nucleic acid sequences described herein can be regulatory regions, such as promoters, "enhancers" or introns containing regulatory elements. Provided herein is a method for using such regulatory regions to modulate seed storage compound metabolism. When the LMR nucleic acids are regulatory regions, the LMR nucleic acids may be used in expression cassettes. An expression cassette comprising a LMR nucleic acid is operably linked to the coding sequence of a nucleic acid sequence of interest such that the LMR regulatory region is capable of controlling expression of the product encoded by the nucleic acid sequence of interest. The seed-specific nature of the wri1 mutant phenotype indicates that the LMR promoter is seed-specific. Therefore, a LMR promoter can be used for the seed-specific expression of other proteins with functions not directly related to the LMR protein. For example, a seed-specific LMR promoter can be used to express proteins that can control events in seed development.

"Enhancers" are cis-acting regulatory sequences that cause increased expression of genes located at a distance away, preferably within 5 kb from the enhancer element. Such enhancers can be used to overexpress other genes of interest with the aim to modulate seed storage compound metabolism. Introns may contain regulatory elements that affect the level of expression, splicing and stability of the RNA transcript. It was discovered that the WRI1 gene contains an unusually large intron of 1650 bp and that some differential RNA splicing products were observed during RT-PCR analysis. Manipulation of the intron size and sequences can be used to modulate the expression level and relative abundance of particular splicing products that have the desired biological activity and lead to desired changes in seed storage compound metabolism. Regulatory sequences such as promoters, enhancers and regulatory elements contained on introns can be found in SEQ ID NO:7 shown in FIG. 6.

The LMR nucleic acids, amino acid sequences, and analogs and fragments thereof, of the present invention have a variety of uses. The nucleic acid molecules encoding the LMR proteins of the invention may be utilized in the genetic engineering of a wide variety of plants to make them better or more efficient producers of one or more seed storage compounds. The LMR proteins described herein are capable of, for example, performing a function involved in the metabolism of compounds necessary for lipid or fatty acid biosynthesis, and may be directly involved in the partitioning of plant resources to the various seed storage compounds, such as fatty acids, lipids, starch or proteins. Therefore the LMR proteins can be used to manipulate the relative proportions of lipids, starch and proteins in seeds. These LMR proteins can also be used to increase the relative proportion of any seed storage compound, such as a storage lipid, without decreasing the abundance of another seed storage compound.

In accordance with the present invention, a transgenic plant is produced that contains a LMR nucleic acid, comprised of elements described above, resulting in the modification of the level of a seed storage compound in the transgenic plant. Described herein is a method of producing a transgenic plant with a modified level of a seed storage compound comprising, transforming a plant cell with an expression vector comprising an LMR nucleic acid and regenerating a plant with a modified level of the seed storage compound from the plant cell. The methods of the present invention involve the introduction of a wild-type or mutant LMR nucleic acid into a cell of the plant, either maintained on a separate plasmid, encoded by a genetically modified replicating plant virus or integrated into the genome of the host cell. If integrated into the genome, such integration can be random, or it can take place by recombination such that the native nucleic acid sequence is replaced by the introduced copy, or by using a LMR nucleic acid in trans such that the nucleic acid is functionally linked to a functional expression unit containing at least a sequence facilitating the expression of a nucleic acid and a sequence facilitating the polyadenylation of a functionally transcribed nucleic acid.

The present invention teaches compositions and methods for modification of the level of a seed storage compound in a plant or seed, and preferably a plant or seed oil, as compared to a wild-type variety of that plant. As used herein, "modification" includes an increase in the level of a seed storage compound, a decrease in the level of seed storage compound, an increase in the transport of a seed storage compound to lipid microbodies and protein storage granules. For example, the compositions and methods of the present invention can be used to increase or decrease the level of a lipid in a seed oil, or to increase or decrease the level of a fatty acid in a seed oil, to increase or decrease the level of a starch in a seed or plant, or to increase or decrease the level of a seed storage protein in a seed or plant.

In one embodiment, a higher-than-normal level of a seed storage compound is produced in a transgenic plant. The term "higher-than-normal level" refers to a level higher than that found in a wild-type variety of the transgenic plant. In a special case, the increased synthesis and accumulation of seed storage lipids caused by the altered expression of a homologous LMR or expression of an altered version of a LMR can be used to increase the yield of polyunsaturated fatty acids like arachidonic acid (ARA) and/or eicosapentaenoic acid (EPA) and/or docosahexaenoic acid (DHA) in transgenic plants that express genes from mosses and algae for the production of these neutraceuticals. Finally, the term "modification" includes the introduction of a new seed storage compound into a plant or seed.

The LMR nucleic acids can be used to modify the relative proportions of plant storage compounds in seeds of transgenic plants. Especially in the case of oilseed plants the ratio of the storage lipids can be modified in relation to the seed protein and seed starch content. The LMR nucleic acids can be utilized to modify the relative proportions of seed storage compounds and also other compounds accumulating in seeds by influencing the partitioning of the photosynthate into the respective biochemical pathways. The implied pathways are responsible for the production of fatty acids for membrane and storage lipids, amino acids for the synthesis of proteins, carbohydrates for the synthesis of starch, or precursors of pathways that lead to the synthesis of a large variety of compounds like isoprenoids, lignin, cellulose, hemicellulose, glucans and pectin.

Modification of the level of a seed storage compound may be achieved by a modification of the metabolism of that compound. The term "metabolism" is art-recognized and includes the totality of the biochemical reactions that take place in an organism. The "metabolism" of a particular compound, then, (e.g., the metabolism of a fatty acid) comprises the overall biosynthetic, modification, and degradation pathways in the cell related to this compound. The terms "biosynthesis" and "biosynthetic pathway" are art-recognized and include the synthesis of a compound, preferably an organic compound, by a cell from intermediate compounds in what may be a multi-step and highly regulated process. The terms "degradation" and "degradation pathway" are art-recognized and include the breakdown of a compound, preferably an organic compound, by a cell to degradation products (smaller or less complex molecules) in what may be a multi-step and highly regulated process.

Also included herein are compositions and methods for the modification of the efficiency of production of a seed storage compound. The term "efficiency of production" includes the time required for a particular level of production to be achieved (for example, how long it takes for the cell to attain a particular rate of output of a seed storage compound). The term "yield" is art-recognized and includes the quantity of product (i.e., seed storage compound or seeds) obtained per surface area (i.e. hectar or acre). This is generally written as, for example, tons product per hectar. By increasing the yield or production of the compound, the quantity of recovered molecules, or of useful recovered molecules, of that compound from a given acreage of cultured land is increased. An improved efficiency of production, or an increased or decreased production of a seed storage compound, may be due to a direct effect of manipulation of a nucleic acid of the invention, or it may be due to an indirect effect of such manipulation.

The present invention allows for the production of a true breeding variety of plants that bear seeds having modified levels of a seed storage compound as compared to a wild-type variety. The term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of a single DNA sequence introduced into a plant variety.

In producing a transgenic plant of the present invention, an expression vector containing the introduced nucleic acid sequence is inserted into protoplasts, intact tissues, such as immature embryos and meristems, callus cultures or isolated cells. Preferably, expression vectors are inserted into intact tissues. General methods of culturing plant tissues are provided, for example, by Miki et al., Procedures for Introducing Foreign DNA into Plants in Methods in Plant Molecular Biology and Biotechnology, p. 67-88, CRC Press, 1993.

Methods for introducing an expression vector into plant tissue include the direct infection or cocultivation of plant tissue with *Agrobacterium tumefaciens* (Horsch et al. 1985, Science 227:1229). Preferably, a disarmed Ti-plasmid is used as a vector for foreign DNA sequences. Most preferred is the use of *Agrobacterium* with split embryonic explants as described by Malone-Schoneberg et al. (1994, Plant Science 103:199-207). Although *Agrobacterium* is a preferred vector, other types of vectors can be used for transformation by procedures such as direct gene transfer, in vitro protoplast transformation, plant virus-mediated transformation and liposome-mediated transformation. Plant transformation can also be performed using particle bombardment, polyethylene glycol mediated DNA uptake or the Silicon Carbide Fiber technique (Freeling and Walbot, The Maize Handbook, Springer Verlag, New York 1993).

The seed-specific nature of the wri1 phenotype indicates that a LMR protein is active in developing seeds, and that the ectopic expression of a LMR protein in other parts of transgenic plants, e.g. leaves, roots or tubers, can be used in a method to modulate the primary carbohydrate metabolism in these plant organs. Therefore, transformation of a plant with a LMR nucleic acid as described herein can facilitate the production of storage compounds like starch, proteins and lipids, in plant organs that do not normally accumulate these compounds. A preferred example is the accumulation of storage lipids in leaves, roots or tubers. In another example, the ectopic expression of a LMR protein leads to increased fatty acid biosynthesis that in turn leads to increased rates of fatty acid degradation. Both the increased rate of fatty acid biosynthesis and the increased rate of fatty acid degradation in leaves or roots can, for example, be used to increase the production and accumulation of polyhydroxyalkanoates (e.g. PHB and PHA) in transgenic cells or plants. Polyhydroxyalkanoates are valuable compounds that can be used as biodegradable plastics from renewable resources.

Another aspect of the invention pertains to a method for producing a seed storage compound. This method involves culturing plant cells, tissues, organs or whole plants containing a vector directing the expression of a LMR nucleic acid molecule of the invention, such that a seed storage compound is produced. In a preferred embodiment, this method further includes the step of obtaining a host cell containing such a vector, in which the cell is transformed with the vector directing the expression of a LMR nucleic acid. In a particularly preferred embodiment, the host cell is from a plant of oil producing species.

The LMR nucleic acids and amino acid sequences can also be used as a research tool in methods that aim at the identification of other regulatory proteins that interact with LMR proteins. The identification of the LMR genes by the mapping and cloning of the WRI1 gene disclosed herein makes possible the utilization of a LMR gene in experiments that will identify proteins that participate in the same or related regulatory pathways. For example, a LMR gene can be used in yeast-two-hybrid screens to identify other proteins that interact with the LMR protein. In another example, a LMR protein can be used in immunoprecipitation experiments that make use of antibodies to co-precipitate a LMR protein and proteins interacting with it, thus leading to the identification of interacting protein partners. The antibodies can either be specific for the LMR protein or they can be specific for epitopes that have been attached to the LMR protein by standard cloning techniques. These targeted experiments can only be performed because the discovery of the identity and function of a LMR gene as described herein.

The promoter of a LMR gene can also be used as a research tool in methods that aim at the identification of other regulatory proteins that interact with a LMR promoter. The identification of the LMR genes by the mapping and cloning of the wri1 gene disclosed herein makes possible the utilization of a LMR gene and its promoter in experiments that will identify additional proteins that participate in the same or related regulatory pathways. The length of plant promoter sequences can vary considerably, but it is safe to say that most of the active elements in plant promoters are located within 3000 nucleotide bases upstream of the gene. Therefore a "LMR promoter" is defined herein as the 3000 nucleotide bases of genomic DNA sequence 5' upstream of a LMR coding region. A LMR promoter can, for example, be used in yeast one-hybrid screens to identify other proteins that interact with elements in the promoter.

In another example, a LMR promoter can be spliced to a reporter gene, for example GUS or GFP. Such a LMR promoter-reporter fusion construct can be transformed into transgenic cells or plants. These transgenic cells or plants can be used in mutant screening experiments to find proteins that bind to a LMR promoter. In such experiments, the altered expression of the reporter gene serves as an indication that the mutated gene encodes a protein that can interact with a LMR promoter. The identity of the mutated gene can be established by standard techniques, e.g. molecular mapping or sequencing the genomic DNA flanking the T-DNA or transposon that has been used to create the mutation. Proteins that interact with a LMR promoter can be used to control the expression and activity of the LMR protein and can thus also be used to control the accumulation, relative proportions and total yield of compounds accumulating in seeds of transgenic plants. These targeted experiments with a LMR promoter can only be performed because the discovery of the identity and function of a LMR gene as described herein.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Map-based Cloning of the wri1 Mutant Gene

The wri1-1 mutation was generated in an *Arabidopsis* Columbia-2 (col-2) background, and to ensure the plants would remain viable and have a consistent phenotype, the wri1-1 plants were backcrossed with wild-type *Arabidopsis* col-2 plants for three generations. The homozygous wri1-1 mutant was maintained by successive selfing of the 3× backcrossed mutant. For mapping, the numerous differences in the DNA sequence between *Arabidopsis* ecotypes Landsberg and Columbia were used and an initial mapping population was generated by crossing wri1-1 in an *Arabidopsis* col-2 background with wild-type Landsberg erecta. The F1 generation was selfed and the F2 generation seed harvested.

For the initial mapping, fifty F2 plants of the cross wri1-1 X Landsberg (ler) that were homozygous for the wri1-1 mutation were used. Those fifty plants allowed wri1-1 to be mapped between the CAPS markers BGL1 and AFC1. A second mapping population consisting of 1000 F2 plants was generated in the same manner as the first with the exception that instead of selecting homozygous wri1-1 plants, the total population, including those plants heterozygous for wri1-1 and homozygous wild-type, was included. This expanded population allowed a finer mapping of wri1-1 without having to sort through the large number of plants that would have been required had a purely wri1-1 homozygous mapping population been used. The wri1-1 mutation causes reduced germination and thus wri1-1 homozygous plants are under represented in the F2 population. As an example, obtaining the original fifty homozygous plants required scoring over four hundred F2 plants.

The F2 population was scored for wri1-1/wri1-1, wri1-1/wt, wt/wt and for the presence of Landsberg or Columbia DNA at the CAPS markers, CDC2BG and TSA1. Three recombinants resulted from the scoring, one between wri1-1 and CDC2BG and two between wri1-1 and TSA1, allowing the wri1 gene to be placed between CDC2BG and TSA1. See Table 3 below. Thus, by scoring both the genotype of the F2 plants as well as whether they are Columbia or Landsberg for a given PCR marker, a region that contained the wri1-1 mutation, and hence a LMR genetic locus, was identified.

TABLE 3

| Marker | Recombinants/Total Scored | BAC Clone | GenBank Accession |
|--------|---------------------------|-----------|-------------------|
| AFC1   | 14/1838                   | F4P12     | AL132966          |
| CDC2BG | 1/1839                    | F24B22    | AL132957          |
| TSA1   | 2/1934                    | T5N23     | AL132970          |
| CFI    | 8/1934                    | T44C9     | AL138650          |
| BGL1   | 72/1934                   | F28O9     | AL137080          |

Example 2

Sequencing of Two Different wri1 Alleles from wri1-1 and wri1-2 *Arabidopsis*

Forty four putative LMR genes were identified in the LMR genetic locus. The genomic DNA of three of the putative LMR genes in wri1-1, wri1-2 and wild-type *Arabidopsis* Col plants was sequenced. Overlapping PCR primers were designed as described below and the same primers were used for the sequencing reactions. The aim was to identify sequence changes in the two wri1 mutants compared to the sequence of the wild-type gene as sequence mismatches found by sequencing of the genomic DNA of the mutants can lead to the identification the true wri1 gene.

Sequence alignments indicated that the wri1 locus contained two mismatches in the wri1-1 and wri1-2 mutants. Further analysis indicated that these mismatches were situated in introns of the putative LMR gene.

Primer Design: 112 primers were designed as 56 primer pairs for PCR and for sequencing of the PCR products. Three samples of *Arabidopsis* genomic DNA were provided, namely wild type, wri1-1 and wri1-2. PCR products were obtained by BPS at the DNA Landmarks facility and sequenced at the same facility. For each of the three DNA samples, 56 PCR products were obtained and a total number of 168 PCR products were sequenced from both ends to give 336 sequences. A high fidelity/proof-reading DNA polymerase was used for the PCR reaction because finding point mutations (EMS mutants) in the mutants was desired. In total, nine assembled sequences (three genes for each of the three DNA samples) were obtained. The primers were as follows.

| Primers for Aintegumenta-like protein (gene = "T12E18.10") | | |
|---|---|---|
| Oligo sequence | Location | SEQ ID NO: |
| ACT TGC CCT TTC TCG TTT C | 2873 | 10 |
| TGT TTG CCT TTC TTG TTC TG | 3364 | 11 |
| TGG ATT TGG GTT TTG TCT TA | 3238 | 12 |
| GCG TGA AAG CAG TTG AG | 3644 | 13 |
| CGA GGC TCA TCT TTG GGA | 3324 | 14 |
| TCT TCC TTT GTC ACT CTC TG | 3858 | 15 |
| CCG ACA CCA TCT TGA AT | 3708 | 16 |
| ATC CGA GCC TCC CAT CTT CC | 4248 | 17 |

-continued

Primers for Aintegumenta-like protein
(gene = "T12E18.10")

| Oligo sequence | Location | SEQ ID NO: |
|---|---|---|
| ATT TCG GAA TTT ACT ACC AA | 4001 | 18 |
| CAA AAC TCT CGC CTC AC | 4629 | 19 |

Example 3

Complementation of Wri1 Mutant with Cosmids Containing Wild-type Genomic DNA

Fine mapping placed the WRI1 gene in a one hundred and fifty five kilobase region between PCR markers TSA1 and CDC2BG on chromosome three of *Arabidopsis thaliana*. After the fine mapping, an overlapping set of cosmid vector constructs was assembled for the purpose of conducting transformation rescue experiments of the wrinkled 1 phenotype (shriveled seeds containing reduced levels of seed storage oils). The cosmids were generated by Knut Meyer, using the pBIC20 binary vector and the HIND III partial digest *Arabidopsis thaliana* genomic DNA (Meyer, K., Leube, M. P. and Grill, E. 1994 A protein phosphatase 2C involved in ABA signal transduction in *Arabidopsis thaliana*. Science 264:1452-1455).

In order to accomplish a cosmid rescue of the wri1-1 seed phenotype, an *Arabidopsis* genomic DNA library, contained in the binary vector pBIC 20 (Meyer, K. et al. 1994 Science 264:1452-1455), was screened using radiolabeled PCR products. The PCR products used as templates for probes were obtained through the amplification of genomic DNA in the region of chromosome three between PCR markers TSA1 and CDC2BG. The PCR products ranged in size from 0.5 kb to 1.5 kb. Primers for amplification were chosen based upon the position of the product, with the goal of designing a probe for every twenty kilobase segment of DNA in the region defined by TSA1 and CDC2BG. The library was plated at a density of 3,000-4,000 bacterial colonies per 150 mm petri plate and colony lifts from nine plates were screened with each probe according to the procedures outlined in Sambrook et al. (1989 Molecular Cloning: A Laboratory Manual $2^{nd}$ Edition (Cold Spring Harbor Laboratory, Cold Spring Harbor, N.Y.)).

Once putative positives were identified, plugs of agar containing bacteria in the region of the signal on the autorad were taken and the bacteria eluted into LB, containing tetracycline (10 mg per liter). Serial dilutions were performed and the bacteria plated to a density of one to three hundred colonies per 100 mm petri plate. Colony lifts were performed and the putative positives re-screened. Colonies corresponding to the positive signals were picked and re-screened again. Once the colonies were confirmed, the plasmid containing the genomic DNA was isolated and cut with the restriction enzyme Hind III. The restriction patterns from different colonies were compared and used to designate its position within the cosmid contig. Overlap between cosmid contigs was determined through Southern blotting and hybridization between cosmids in neighboring contigs. Plasmid miniprep products were used to transform *Agrobacterium tumefaciens*, which were then used to transform wrinkled 1-1 plants by dipping. Transformed plants were obtained by selection on kanamycin plates containing cla-vamox to suppress growth of the transformed *Agrobacterium*. The transformed plants were then transferred to soil and the seed of the adult plants scored for rescue of the wrinkled 1 phenotype. See FIG. 2 for a diagram of the cosmid complementation strategy and cosmid clone overlap.

These overlapping cosmids were transformed individually into the *Arabidopsis* wri1-1 mutant described in Example 1 and transformants were scored for restoration of the wild-type seed phenotype (normal seeds with wild-type levels of seed storage oils). Transgenic seedlings that were resistant to the antibiotic selection marker were grown in soil to maturity. Seeds of single siliques were harvested from transformed plants and scored visually for rescue of the wri1-1 shrunken, shriveled phenotype. All of the cosmids corresponding to BAC clones CDC2B and TSA1 were used to transform wri1-1 and none of them recovered the shriveled seed phenotype of the wri1-1 mutation. The cosmids designated as AG1, AG2, AG3 and AG5 rescued the wri1 phenotype and restored seed oil content to near wild type levels. (Cosmid clone AG4 was never transformed, because results from the other clones became available.) For these cosmids the transgenic T2 seeds segregated in a 3:1 ratio of smooth and normal size seeds to shrunken and shriveled seeds, indicating the seeds were heterozygous for the wild type insert of the rescuing fragment of DNA. The seeds of rescued wri1-1 plants were also analyzed by GC and compared to wild type and wri1-1 (see data below). In all cases, seeds that were visually scored as being rescued had an elevated level of TAG. Control plants containing either empty vector or cosmids containing inserts to other regions of the area near the WRI1 locus displayed no increase in TAG content and were visibly indistinguishable from wri1-1. Restoration of the wild-type seed phenotype implied that the complementing cosmids encode the wild-type LMR and thus lead to the identification of the LMR gene.

Determination of the T2 seed lipid content of complementing cosmids

| Genotype | μg of total fatty acids per seed |
|---|---|
| Col-2 wild-type seeds | 10.65 |
| wri1-1 mutant seeds | 2.1 |
| AG1 transgenic seeds | 10.7 |
| AG2 transgenic seeds | 10.63 |
| AG5 transgenic seeds | 9.44 |
| 3P3 transgenic seeds* | 1.5 |
| cdc16-2 transgenic seeds* | 1.7 |
| BPS empty vector transgenic seeds* | 3.1 |

*3P3 and cdc16-2 represent cosmids from the CDC2B region on BAC F24B22 (see FIG. 2) that were transformed into the wri1-1 mutant plants and BPS is the empty vector transgenic control.

The insert sizes of the rescuing cosmids are: AG1 16.05 kb, AG2 19.35 kb, AG3 15.1 kb, AG4 18 kb, AG5 14.6 kb. Table 4 indicates the exact location of the cosmid clones on the BAC genomic sequence. Though not accurately depicted in FIG. 2, the region of overlap between the rescuing cosmids is 8.5 kb, indicating that the WRI1 gene is contained within that 8.5 kb region.

TABLE 4

| Cosmid name | Location on BAC F24B22 (bp) | Location on BAC T12E18 (bp) * | Cosmid size (kb) |
|---|---|---|---|
| AG1 | | 0–16,146 | 16.1 |
| AG2 | | 0–19,450 | 19.4 |

TABLE 4-continued

| Cosmid name | Location on BAC F24B22 (bp) | Location on BAC T12E18 (bp) * | Cosmid size (kb) |
|---|---|---|---|
| AG3 | 90,033–96,928 | 0–8,522 | 15.1 |
| AG4 | 87,481–96,928 | 0–8,522 | 18 |
| AG5 | 89,877–96,928 | 0–8,522 | 14.6 |

* SEQ NO 6 contains the partial genomic sequence on BAC T12E18.

The procedures adhered to in the above experiment are as follows:

PCR for Production of Radio-labeled Probes to Identify Cosmid Clones

PCR for production of radio-labeled probes was performed with the listed primers under the following conditions:

| Denature | 95° C. for 4 minutes |
|---|---|
| Melt | 95° C. for 0.5 minutes |
| Anneal | 55° C. for 0.5 minutes |
| Elongate | 72° C. for 1.5 minutes |
| Repeat the last three steps twenty nine times | |
| Elongate | 72° C. for 10 minutes |
| Hold | 4° C. |

Annealing temperatures for specific primers are listed below with the primer sequence where they differ from the above protocol.

```
PCR Primers for production of radio-labeled
probes:
CDC2BG
CGT CTG AAG GTC TGC ACC TAG TC      SEQ ID NO:20
CGC TAA GAT ACT TCC ACG TCA C       SEQ ID NO:21

RNA binding protein-like, anneal at 54° C.
TGA TGG CTG CGA TGA CT              SEQ ID NO:22
(position 59701 on BAC clone F24B22)
TTC CAC CAT AAC TGC GTC TA          SEQ ID NO:23
(position 60862 on BAC clone F24B22)

Aintegumenta-like protein (gene = "T12E18.10"),
anneal at 54.3° C.
ACT TGC CCT TTC TCG TTT C           SEQ ID NO:24
(position 2873 on BAC clone T12E18)
TGT TTG CCT TTC TTG TTC TG          SEQ ID NO:25
(position 3363 on BAC clone T12E18)

Vicinity of Nucleoid DNA binding-like, anneal at
52.8° C.
TGA TTA CCT GGG CAC ATA             SEQ ID NO:26
(position 24683 on BAC clone T12E18)
CAA AAG AAT GCG AGA CAA             SEQ ID NO:27
(position 25751 on BAC clone T12E18)

Oligopeptide transporter-like, anneal at 53.2° C.
CGC TGC CCT TTC AT                  SEQ ID NO:28
(position 27312 on BAC clone T14E10)
CGC AAT CCT CTC TCT ATG GT          SEQ ID NO:29
(position 28856 on BAC clone T14E10)

T14E10 52K, anneal at 52° C.
TTA TAC GGC TGG GAG ATA             SEQ ID NO:30
(position 52556 on BAC clone T14E10)
GGG CAG TCA AAC AGG TA              SEQ ID NO:31
(position 53602 on BAC clone T14E10)

T14E10 60K, anneal at 52° C.
TAT CTG GAT TCT TCT CT GGG          SEQ ID NO:32
(position 45037 on BAC clone T14E10)
ATC AGG GAG CTT GAT TTT GG          SEQ ID NO:33
(position 47495 on BAC clone T14E10)

TSA1
TCT TGG TAG CAT GAT TCT CAG TC      SEQ ID NO:34
(end of BAC clone T14E10)
CCT TTC CCG CTT ACA GAT GAT C       SEQ ID NO:35
(end of BAC clone T14E10)
```

Media

Media for bacteria culture consisted of Luria-Bertani (LB) Medium (Sambrook et al. 1989 Molecular Cloning: A Laboratory Manual $2^{nd}$ Edition Cold Spring Harbor Laboratory, Cold Spring Harbor, N.Y.), with or without agar (1.2% if with), and the appropriate antibiotic (10 mg per liter of tetracycline for *Escherichia coli* containing pBIC20 and 50 mg per liter of kanamycin for *Agrobacterium tumefaciens* containing pBIC20). Media for plants consisted of 0.5× MS (sigma M5524) containing 2% sucrose and 1.2% agar at a pH of 5.8-6.0 with 5 M KOH. After the media had cooled to approximately 45° C., kanamycin was added to a concentration of 50 mg per liter.

Plating of the Cosmid Library and Selection of Cosmids by Colony-blotting

The library was plated by scraping a piece of the frozen culture out of the stock tube and then diluting the frozen piece in 1 ml of liquid LB with tetracycline. Serial dilutions were performed and the amount of bacteria per 0.001 ml volume determined. The volume that contained 3,000-4,000 bacteria was then placed onto a 120 mm diameter petri plate and 0.6 ml of liquid LB with tetracycline was added to aid in spreading the bacteria.

Plugs from the library were taken by using the large end of a blue pipette to remove a circle of media corresponding to a positive signal on an autorad from a colony lift of a plate containing the bacteria bearing the DNA that hybridized to the probe used. The plug was then placed into a 1.5 ml centrifuge tube, containing 0.6 ml of liquid LB. The tube was vortexed and serial dilutions done until the original solution with the plug had been diluted ten thousand-fold. From the 10-4 dilution, 0.005 and 0.010 ml were taken and plated using 0.050 ml of liquid LB to assist in spreading the bacteria onto 100 mm petri plates containing LB with agar and tetracycline.

Plates that contained approximately 300 colonies were then used to further isolate the bacteria containing the cosmid of interest by doing colony lifts, probing the filters and then picking off the bacteria from the region that contained a hybridizing colony. The individual colony was then grown up, the cosmid isolated, cut with Hind III and the restriction pattern compared to other cosmids.

*Agrobacterium Transformation*

*Agrobacterium tumefaciens* was transformed with the selected cosmid binary vectors by electroporation in a 0.2 cm cuvette. The electroporator was set to 25 µF, 200 ohm, and 2.5 V. After electroporation, the bacteria were grown for one hour in liquid LB without antibiotics and then the entire culture was transferred into a culture flask containing liquid LB and the appropriate antibiotics.

Plant Transformation

*Agrobacterium tumefaciens* cultures were grown overnight, spun down at 4000 rpm for ten minutes and resuspended in 30 ml of 5% sucrose. The bacteria were then transferred to 300 ml of 5% sucrose containing 0.3 ml of Silwet surfactant (Lehle Seeds, catalog #vis-01). Pots containing 20 wri1-1 plants, which were just starting to bolt, were dipped and swirled in the solution for at least thirty seconds and then placed on their sides in a covered flat. Three pots, each of plants, were dipped with each construct. The dipped plants were grown in plant growth chambers and seeds were harvested.

Selection of Transgenic Plants Containing Cosmid Binary Vector Constructs

Seeds from dipped plants were surface sterilized using a 20% solution of bleach (Clorox) and 0.2% triton×100. Approximately 2,000 seeds were incubated in a 1.5 ml centrifuge tube, containing 1.2 ml of the solution, with gentle agitation for twenty minutes and then rinsed in a sterile environment with sterile water. The seeds were rinsed by adding one ml of water to the seeds. The seeds were then allowed to settle, the water removed and more water added. This procedure was performed a total of six times. *Arabidopsis* seeds were plated on MS plates containing kanamycin and clavamox to suppress growth of the transformed *Agrobacterium*. Kanamycin resistant transgenic plants (transformants) were selected and transferred to soil. Plants were grown in plant growth chambers.

Scoring the Seed Phenotype of Transgenic Plants to find Complementing Cosmids and Confirmation of the Identity of an LMR Gene Individual mature siliques from each transformant are visually and microscopically scored for rescue of the wri1-1 phenotype. Seeds from transgenic wri1-1 plants containing the complementing cosmid exhibit wild-type seed phenotype and can be differentiated from wri1-1 seeds. Depending on the specific complementing cosmid, the choice of possible LMR candidate genes will be reduced drastically and the most important LMR can be identified. This cosmid rescue experiment can be followed by complementation with binary vectors containing individual cDNAs of the LMR candidates to identify unambiguously the LMR that causes the wri1 phenotype in the wri1-1 mutant. Additionally, the wri1-1 and wri1-2 genomic DNA encoding this LMR can be sequenced to determine the genetic lesions of the LMR gene in these two mutants.

Example 4

Cloning of WRI1 by RT-PCR

Transformation of the wri1-1*Arabidopsis* mutant with cosmid binary vectors (Example 3) containing genomic sequences spanning the region identified by molecular mapping (Example 1) lead to the discovery of 4 overlapping cosmids that complemented the wri1-1 mutant and restored the wild-type seed phenotype and seed oil content (FIG. 2 and Example 3). The smallest common genomic fragment on the 4 complementing cosmid binary vectors is 8.5 kb, indicating that the WRI1 gene is contained within that 8.5 kb region. According to the automatically generated annotation of the genomic sequence in GenBank this 8.5 kb fragment fully contains two open reading frames (ORFs, SEQ ID NOs:8 and 9) and the partial fragments of another two ORFs. However, by using RT-PCR we discovered that the two ORFs (SEQ ID NOs:8 and 9) are actually part of the same gene containing an unusually long intron of 1641 nucleotides. Based on the wri1 mutant and our mapping data we named this gene "WRI1". The WRI1 RT-PCR product was 1.6 kb long. The amplification of a 3.8 kb genomic PCR product in the RT-RCR reactions that were not DNAse-treated indicated that the 1.6 kb RT-PCR product was really derived from a 1.6 kb mRNA transcript. The RT-PCR products derived from the wri1-1 mutant showed a small increase in size compared to wild type and the wri1-2 mutant. It is possible that differential splicing of the mRNA transcript can lead to such transcript size differences.

A full-length WRI1 cDNA was isolated by RT-PCR using a proof-reading polymerase (Method described in Example 5) and its nucleotide sequence was determined (SEQ ID NO:1). The primers used in this reaction were as follows: GGT ACC AAA TCT AAA CTT TCT CAG AG (SEQ ID NO:36), ACT AGT AAA TCT AAA CTT TCT CAG AG (SEQ ID NO:37), TCT AGA AAA TCT AAA CTT TCT CAG AG (SEQ ID NO:38) and TCT AGA GGC AAA GAC ATT GAT TAT TC (SEQ ID NO:39). The cDNA encoded by this gene is 1539 bp long, has a 166 bp 3' UTL and contains a 1293 bp ORF (SEQ ID NO:2) encoding a protein of 430 amino acids (SEQ ID NO:3). The WRI1 cDNA encoded protein sequence shows slight sequence similarity to a known transcription factor, Ainteguments, and contains an Apetala-2-like DNA binding domain. Therefore we propose that WRI1 acts as a transcription factor regulating lipid and seed storage compound metabolism during seed development.

Example 5

Cloning of *Arabidopsis* cDNAs Encoding LMR Proteins

The *Arabidopsis* LMR partial or full-length cDNA can be obtained by RT-PCR using total RNA from developing *Arabidopsis* siliques. The essential LMR-specific PCR primers located upstream of the start codon and downstream of the stop codon can be designed based on the availability of the genomic DNA sequence. The mapping of the wri1 LMR genetic locus as described in Example 1 is of crucial importance for this, as it indicated which genomic DNA sequence has to be used for this purpose.

Total RNA can be isolated from *Arabidopsis thaliana* developing seeds or siliques by the method of Van Slogteren (1983, Plant Mol. Biol. 2:321-333) with slight modifications. For this method, the developing silique tissue (200 mg) is frozen with liquid nitrogen and ground to a fine powder with a mortar and pestle. The powder is placed in a microfuge tube and the RNA extracted with 500 µl of extraction buffer (phenol: 0.1M LiCl, 100 mM Tris-HCl [pH8.0], 10 mM EDTA, 1% SDS (w/v) [1:1]) pre-heated to 90° C. The mixture is heated further for 1 minute at 90° C. and then vortexed for 5 minutes. Proteins are extracted by adding 250 µl of chloroform:isoamyl alcohol (24:1) and the mixture is vortexed for 5 minutes and centrifuged for 44 minutes at 13,000 rpm in an Eppendorf centrifuge 5414 at 4° C. The aqueous layer is removed and the protein extraction repeated twice more.

One volume of 4 mM LiCl is added and the RNA is allowed to precipitate overnight at 4° C. To collect the RNA, the mixture is centrifuged for 44 minutes at 4° C. at 13,000 rpm in an Eppendorf centrifuge 5414. The pellet is re-suspended in 250 µl sterile, deionized water. To precipitate the RNA, 0.1 volumes of 3M sodium acetate (pH 5.2) and 2 volumes 100% ethanol are added. An aliquot is taken and centrifuged for 20 minutes at 4° C. at 13,000 rpm in an Eppendorf centrifuge 5414. The pellet is washed with 70% ethanol to remove salts from the pellet and dried using a speed vac. The pellet is re-suspended in 25 µl DEPC-treated H₂O and analyzed for integrity via electrophoresis. The RNA is stored at −70° C.

For the RT-PCR and cloning of *Arabidopsis* LMR genes, the synthesis of the first strand cDNA is achieved using AMV Reverse Transcriptase (Roche, Mannheim, Germany). The resulting single-stranded cDNA is amplified via Polymerase Chain Reaction (PCR) utilizing the two gene specific primers. The conditions for the reaction are standard conditions described in the Expand High Fidelity PCR system (Roche). The parameters for the reaction are: five minutes at 94° C. followed by five cycles of 40 seconds at 94° C., 40 seconds at 50° C. and 1.5 minutes at 72° C. This is followed by thirty cycles of 40 seconds at 94° C., 40 seconds at 65° C. and 1.5 minutes at 72° C.

The fragment is extracted from agarose gel with a QIAquick Gel Extraction Kit (Qiagen) and ligated into a cloning vector, for example the TOPO pCR 2.1 vector (Invitrogen), following the manufacturer's instructions. Recombinant vectors are transformed into Top10 cells (Invitrogen) using standard conditions. Transformed cells are selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies are selected and used to inoculate 3 ml of liquid LB containing 100 µg/ml ampicillin and grown overnight at 37° C. Plasmid DNA is extracted using the QIAprep Spin Miniprep Kit (Qiagen) following manufacturer's instructions.

The RT-PCR cloned *Arabidopsis* LMR gene is sequenced to verify that the complete cDNA sequence corresponds with the genomic sequence (SEQ ID NO 6). The fragment containing the *Arabidopsis* LMR cDNA is excised from the recombinant PCR2.1 TOPO vector by digestion with restriction enzymes according to manufacturer's instructions. The subsequent fragments are excised from an agarose gel with the QIAquick Gel Extraction Kit (QIAgen) according to manufacturer's instructions and ligated into the plant binary vector used for over expression of the gene in *Arabidopsis*.

The plant binary vector is constructed by digestion with restriction enzymes. A DNA fragment encoding the LMR gene is cloned into the binary vector between a promoter and a terminator so that a functional LMR protein can be expressed by this construct. The construct also contains antibiotic resistance marker genes that enable the selection of the binary vector in *E. coli*, *Agrobacterium* and in transgenic plants, respectively.

Example 6

Cloning and Sequencing of wri1-1 and wri1-2 Allelic cDNAs

The isolation and sequencing of the allelic wri1 cDNAs of the wri1-1 and wri1-2 mutants will pinpoint the changes in the WRI1 gene sequence that lead to the phenotype in the mutants. Both mutants are able to express the mutated gene and show a RT-PCR band of approximately the right size (Example 4). The RT-PCR products obtained from the wri1-1 mutant was sequenced at it was determined that the sequence contains a point mutation at a position corresponding to nucleotide 3197 of the T12E18 BAC sequence shown in SEQ ID NO:7 and FIG. 6. This point mutation resulted in a G to A conversion in the intron splicing site of the wri1-1 gene such that the mutant wri1-1 mRNA is no longer spliced correctly and the ORF continues until a stop codon is reached in the intron. This altered splicing results in a truncated and non-active form of the WRI1 protein. These same procedures are followed to identify the mutation(s) in the wri1-2 gene.

Example 7

Plasmids for Plant Transformation

For plant transformation, binary vectors such as pBinAR can be used (Höfgen and Willmitzer, 1990, Plant Science 66:221-230). Construction of the binary vectors can be performed by ligation of the cDNA in sense or antisense orientation into the T-DNA. 5-prime to the cDNA, a plant promoter activates transcription of the cDNA. A polyadenylation sequence is located 3-prime to the cDNA.

Tissue specific expression can be achieved by using a tissue specific promoter. For example, seed specific expression can be achieved by cloning the napin or LeB4 or unknown seed protein (USP) promoter 5'-prime to the cDNA. Also, any other seed specific promoter element can be used. For constitutive expression within the whole plant, the CaMV 35S promoter can be used.

The expressed protein can be targeted to a cellular compartment using a signal peptide, for example for plastids, mitochondria or endoplasmic reticulum (Kermode 1996, Crit. Rev. Plant Sci. 44,4:285-423). The signal peptide is cloned 5-prime in frame to the cDNA to archive subcellular localization of the fusion protein.

Example 8

*Agrobacterium* Mediated Plant Transformation

*Agrobacterium* mediated plant transformation with the LMR nucleic acids described herein can be performed using standard transformation and regeneration techniques (Gelvin, Stanton B. and Schilperoort, Robert A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993). For example, *Agrobacterium* mediated transformation can be performed using the GV3 (pMP90) (Koncz and Schell 1986, Mol. Gen. Genet. 204: 383-396) or LBA4404 (Clontech) *Agrobacterium tumefaciens* strain.

*Arabidopsis thaliana* can be grown and transformed according to standard conditions (Bechtold 1993, Acad. Sci. Paris. 316:1194-1199; Bent et al. 1994, Science 265:1856-1860). Additionally, rapeseed can be transformed with the LMR nucleic acids of the present invention via cotyledon or hypocotyl transformation (Moloney et al., 1989, Plant cell Report 8:238-242; De Block et al., 1989, Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. Additionally, Agrobacterium mediated gene transfer to flax can be performed using, for example, a technique described by Mlynarova et al. (1994, Plant Cell Report 13:282-285).

Transformation of soybean can be performed using for example a technique described in EP 0424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

The method of plant transformation is also applicable to Brassica and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

Agrobacterium tumefaciens culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and re-suspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced Agrobacterium suspension culture. (The imbibition of dry embryos with a culture of Agrobacterium is also applicable to maize embryo axes).

The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 440 µmol m$^{-2}$sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol m$^{-2}$sec$^{-1}$ light intensity and 12 hours photoperiod for about 80 days.

Samples of the primary transgenic plants (T0) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

Example 9

Northern Blots of Developing Seeds from *Arabidopsis Mutants* and from Wild Type *Arabidopsis*

Northern blot analysis of the expression levels of LMR gene transcripts in developing seeds of wild-type *Arabidopsis* and the wri1-1 and wri1-2 mutants is done according to standard procedures (Sambrook et al. 1989). Significant differences in the expression levels of a LMR gene are not expected in the case of EMS-induced point mutations in a LMR gene that lead to a frame-shift or that introduce a premature stop codon except in the following cases. Firstly, the absence of LMR mRNA transcripts in the wri1 mutants compared to the wild-type can indicate that the EMS-induced mutation occurred in critical parts of the LMR promoter or in the transcription initiation site. Secondly, significant observable differences in the expression levels of a LMR gene between the wild-type and the wri1 mutants can indicate that transcription of the LMR gene is subject to up- or down-regulation as part of the regulatory mechanism in which the LMR also partakes. For example, a mechanism that senses the lack of accumulation of storage compounds in developing seeds can cause the up-regulation of positive LMR genes upstream in the regulatory cascade, or the down-regulation of a negatively acting LMR gene upstream in the regulatory cascade. This will be further evidence of the essential function of a LMR protein in the seed metabolism and in particular the accumulation of seed storage compounds. Finally, the size of the mRNA transcript of the mutant LMR gene can be changed because of the mutation, indicating that the EMS-induced mutation in the wri1 gene causes incorrect splicing of the mRNA transcript, which in turn leads to the malfunctioning of the WRI1 protein.

Example 10

Assessment of the Expression and Activity of a Recombinant LMR Protein

The expression of a recombinant LMR protein can be assessed at the transcriptional level using Northern blots as are well known to those of skill in the art and as described in Example 9 above. To assess the presence or relative quantity of protein translated from this mRNA, standard techniques, such as a Western blot, may be employed. Additionally, the activities and kinetic parameters of enzymes can be determined by methods well established in the art. Experiments to determine the activity of any given altered enzyme must be tailored to the specific activity of the wild-type enzyme, which is well within the ability of one skilled in the art.

The activity of LMR proteins that bind to DNA can be measured by several well-established methods, such as DNA band-shift assays (also called gel retardation assays). The effect of such LMR proteins on the expression of other molecules can be measured using reporter gene assays (such as that described in Kolmar, H. et al., 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of LMR membrane-transport proteins can be performed according to techniques such as those described in Gennis R. B., 1989, Pores, Channels and Transporters, in Biomembranes, Molecular Structure and Function, Springer: Heidelberg, pp. 85-137, 199-234 and 270-322.

Example 11

Seed-specific Expression of an LMR Promoter

The promoter region of a LMR gene is cloned into a binary vector, driving the reporter gene GUS (Jefferson et al., 1987). The resulting construct is transformed into Arabidopsis plants as described in Example 8. The activity of the promoter in developing seeds is assayed by GUS staining.

Example 12

Analysis of the Impact of the Transformation of a Plant with Recombinant LMR Nucleic Acids on the Production of a Desired Seed Storage Compound from the Plant The effect of the genetic modification in plants or on production of a desired seed storage compound (such as a fatty acid) therein can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al., 1987 Applications of HPLC in Biochemistry in: Laboratory Techniques in Biochemistry and Molecular Biology, vol. 17; Rehm et al., 1993, Product recovery and purification, Biotechnology, vol. 3, Chapter III, pp. 469-714, VCH: Weinheim; Belter, P. A. et al. 1988, Bioseparations: downstream processing for biotechnology, John Wiley and Sons; Kennedy, J. F. and Cabral, J. M. S. 1992, Recovery processes for biological materials, John Wiley and Sons; Shaeiwitz, J. A. and Henry, J. D., 1988, Biochemical separations in: Ulmann's Encyclopedia of Industrial Chemistry, Separation and purification techniques in biotechnology, vol. B3, Chapter 11, pp. 1-27, VCH: Weinheim; and Dechow, F. J. 1989).

Besides the above-mentioned methods, plant lipids are extracted from plant material as described by Cahoon et al. (1999, Proc. Natl. Acad. Sci. USA 96,22:12935-12940) and Browse et al. (1986, Analytic Biochemistry 442:141-145). Qualitative and quantitative lipid or fatty acid analysis is described in Christie, William W., Advances in Lipid Methodology. Ayr/Scotland: Oily Press.—(Oily Press Lipid Library; 2); Christie, William W., Gas Chromatography and Lipids. A Practical Guide—Ayr, Scotland: Oily Press, 1989 Repr. 1992.—IX,307 S.—(Oily Press Lipid Library; 1); "Progress in Lipid Research, Oxford: Pergamon Press, 1(1952)—16(1977) u.d.T.: Progress in the Chemistry of Fats and Other Lipids CODEN.

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves" Methods Enzymol. 174: 518-552; for other methods see also Härtel et al. 1998, Plant Physiol. Biochem. 36: 407-417 and Focks & Benning 1998, Plant Physiol. 118: 91-101).

For the extraction of soluble sugars and starch, 50 seeds are homogenized in 500 µl of 80% (v/v) ethanol in a 1.5-ml polypropylene test tube and incubated at 70° C. for 90 min. Following centrifugation at 16,000 g for 5 min, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µl of 0.2 N KOH, and the suspension is incubated at 95° C. for 1 h to dissolve the starch. Following the addition of 35 µl of 1 N acetic acid and centrifugation for 5 min at 16,000 g, the supernatant is used for starch quantification.

To quantify soluble sugars, 10 µl of the sugar extract is added to 990 µl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoiso-merase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding" Anal. Biochem. 72: 248-254). For quantification of total seed protein, 15-20 seeds are homogenized in 250 µl of acetone in a 1.5-ml polypropylene test tube. Following centrifugation at 16,000 g, the supernatant is discarded and the vacuum-dried pellet is resuspended in 250 µl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 min and 200 ml of the supernatant will be used for protein measurements. In the assay γ-globulin is used for calibration. For protein measurements Lowry DC protein assay (Bio-Rad) or Bradford-assay (Bio-Rad) are used.

Enzymatic assays of hexokinase and fructokinase are performed spectrophotometrically according to Renz et al. (1993, Planta 190: 156-165), of phosphogluco-isomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194: 95-101) and of UDP-Glucose-pyrophosphorylase according to Zrenner et al. (1995, Plant J. 7: 97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36: 407-417) and metabolites are measured as described in Jelitto et al. (1992, Planta 188: 238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (O'Fiehn et al. 2000, Nature Biotechnology 18:1447-1161).

Unequivocal proof for the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998).

Material to be analyzed can be disintegrated via sonification, glass milling, liquid nitrogen and grinding or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 minutes at 240° C. The identity of resulting fatty acid methylesters is defined by the use of standards available form commercial sources (i.e., Sigma).

In case of fatty acids where standards are not available, molecule identity is shown via derivatization and subsequent GC-MS analysis. For example, the localization of triple bond fatty acids is shown via GC-MS after derivatization via 4,4-Dimethoxyoxazolin-Derivaten (Christie, 1998).

Example 13

Purification of a LMR Protein from a Transgenic Plant

An LMR protein can be recovered from a plant cell (or any other host cell) or cell supernatant using various methods well known in the art. If the LMR protein is secreted from the desired cells, then the cells are removed from the culture by low-speed centrifugation, and the supernatant fraction is retained for further purification. If the LMR protein is not secreted from the cells, it can be harvested from the culture by low-speed centrifugation and then lysed by standard techniques, such as mechanical force or sonification. A LMR protein can also be isolated from plant organs and tissues. Organs of plants can be separated mechanically from other tissue or organs prior to isolation of the seed storage compound from the plant organ. Following homogenization of the plant material, cellular debris is removed by centrifugation, and the supernatant fraction containing the soluble proteins is retained for further purification of the desired LMR protein.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One of ordinary skill in the art is well versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to those of skill in the art and the preceding method of purification is not meant to be limiting. Such purification techniques are described, for example, in Bailey, J. E. & Ollis, D. F. Biochemical Engineering Fundamentals, McGraw-Hill, New York 1986.

The identity and purity of the isolated LMR proteins may be assessed by techniques standard in the art. These include high-performance liquid chromatography (HPLC), spectroscopic methods, staining methods, thin layer chromatography, NIRS, enzymatic assay and microbiological methods. Such methods of analysis are reviewed by Patek et al. (1994 Appl. Environ. Microbiol. 60:133-140), Malakhova et al. (1996 Biotekhnologiya 11:27-32), Schmidt et al. (1998 Bioprocess Engineer. 19:67-70), Ulmann's Encyclopedia of Industrial Chemistry (1996 vol. A27, VCH: Weinheim, pp. 89-90, 521-540, 540-547, 559-566, 575-581 and 581-587), Michal, G. (1999 Biochemical Pathways: An Atlas of Biochemistry and Molecular Biology, John Wiley and Sons) and Fallon, A. et al. (1987 Applications of HPLC in Biochemistry in: Laboratory Techniques in Biochemistry and Molecular Biology, vol. 17).

Example 14

Identification of LMR Protein Orthologs in Soybean, Brassica, Sunflower and Corn The nucleic acid sequences of the *Arabidopsis* LMR proteins can be used to find orthologs in other plant species. The aim is to find LMR proteins that are expressed in seeds or in storage organs like tubers. Since *Arabidopsis* LMR proteins play a central role in the regulation of the accumulation seed storage lipids, it is expected that the LMR protein orthologs in other plant species will play an equally important and similar role. Sequence homologies (identities and similarities) can be used to find these orthologs by using the methods described above, and in particular, by searching sequence databases with search algorithms like FASTA, TBLASTN or those disclosed in the above description. Sequence-similarity searches can be performed on public or proprietary sequence database and the identification of the *Arabidopsis* LMR orthologs in other plant species can be followed-up with the cloning of the partial or full-length cDNAs encoding these LMR orthologs.

Alternatively, the complement of all transcripts present in developing seeds or storage organs, represented by for example cDNA libraries, can be screened by hybridization to find genes similar to the *Arabidopsis* LMR nucleic acids. The *Arabidopsis* LMR nucleic acids or short fragments thereof, or oligonucleotide probes based on the *Arabidopsis* LMR nucleic acids can be used for this purpose. Screening by hybridization can be performed by using standard protocols (Sambrook et al., 1989). These procedures will allow the identification of partial or full-length cDNA clones of LMR genes of other plant species.

Example 15

In Vivo Mutagenesis

In vivo mutagenesis of LMR nucleic acids can be performed by incorporation of a LMR nucleic acid into a plasmid (or other vector) and passage of the plasmid through *E. coli* or other microorganism (e.g. Bacillus spp. or yeasts such as *Saccharomyces cerevisiae*) that is impaired in its capability to maintain the integrity of its genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277-2294, ASM Washington). Such strains are well known to those skilled in the art. The use of such strains is illustrated, for example, in Greener, A. and Callahan, M., 1994, Strategies 7:32-34.

Transfer of mutated LMR nucleic acids into plants is preferably done after selection and testing in microorganisms. Transgenic plants are generated according to various examples within the exemplification of this document.

---

The invention claimed is:

1. An isolated Lipid Metabolism Regulator (LMR) nucleic acid comprising a polynucleotide sequence selected from the group consisting of:
   a) a full-length polynucleotide as shown in SEQ ID NO:4;
   b) a full-length polynucleotide as shown in SEQ ID NO:5;
   c) a polynucleotide encoding a full-length polypeptide as shown in SEQ ID NO:6;
   d) a polynucleotide having at least 95% sequence identity with the full-length polynucleotide of any of a) through b) above;
   e) a polynucleotide encoding a polypeptide having at least 95% sequence identity with the polypeptide of c) above; and
   f) a polynucleotide complementary to a full-length polynucleotide of any of a) through e) above;
wherein expression of the LMR nucleic acid in a plant results in an increased level of a lipid in the plant as compared to a control plant, and wherein the control plant has not been transformed with the LMR nucleic acid.

2. The isolated LMR nucleic acid of claim 1, wherein the nucleic acid comprises a full-length polynucleotide as shown in SEQ ID NO:4.

3. The isolated LMR nucleic acid of claim 1, wherein the nucleic acid comprises a full-length polynucleotide as shown in SEQ ID NO:5.

4. The isolated LMR nucleic acid of claim 1, wherein the nucleic acid comprises a polynucleotide encoding a full-length polypeptide as shown in SEQ ID NO:6.

5. A recombinant expression vector comprising the LMR nucleic acid of claim 1, wherein expression of the vector in a host cell increases the level of a lipid in the host cell.

6. The recombinant expression vector of claim 5, wherein the host cell is a plant cell.

7. A transgenic plant cell comprising the LMR nucleic acid of claim 1.

8. The transgenic plant cell of claim 7, wherein expression of the LMR nucleic acid in the plant cell results in an increased level of a lipid in the plant cell as compared to a control plant cell, and wherein the control plant cell has not been transformed with the LMR nucleic acid.

9. A transgenic plant comprising the LMR nucleic acid of claim 1.

10. The transgenic plant of claim 9, wherein the plant is a dicotyledonous plant.

11. The transgenic plant of claim 9, wherein the plant is a monocotyledonous plant.

12. The transgenic plant of claim 9, wherein the plant is selected from the group consisting of rapeseed, canola, linseed, soybean, sunflower, maize, oat, rye, barley, wheat, pepper, tagetes, cotton, oil palm, coconut palm, flax, castor and peanut.

13. The transgenic plant of claim 9, wherein expression of the LMR nucleic acid in the plant results in an increased level of a lipid in the plant as compared to a control plant, and wherein the control plant has not been transformed with the LMR nucleic acid.

14. A seed produced by the trausgenic plant of claim 13, wherein the plant is true breeding for an increased level of a lipid as compared to a control plant, and wherein the control plant has not been transformed with the LMR nucleic acid.

15. A method of producing a transgenic plant having an increased level of a lipid comprising the steps of transforming a plant cell with an expression vector comprising a Lipid Metabolism Regulator (LMR) nucleic acid and generating from the plant cell the transgenic plant, wherein the LMR nucleic acid comprises a polynucleotide selected from the group consisting of:
   a) a full-length polynucleotide as shown in SEQ ID NO:4;
   b) a full-length polynucleotide as shown in SEQ ID NO:5;
   c) a polynucleotide encoding a full-length polypeptide as shown in SEQ ID NO:6;
   d) a polynucleotide having at least 95% sequence identity with the full-length polynucleotide of any of a) through b) above;
   e) a polynucleotide encoding a polypeptide having at least 95% sequence identity with the full-length polypeptide of c) above; and f) a polynucleotide complementary to a full-length polynucleotide of any of a) through e) above;

wherein expression of the LMR nucleic acid in a plant results in an increased level of a lipid in the plant as compared to a control plant, and wherein the control plant has not been transformed with the LMR nucleic acid.

16. The method of claim 15, wherein the LMR nucleic acid comprises a full-length polynueleotide as shown in SEQ ID NO:4.

17. The method of claim 15, wherein the LMR nucleic acid comprises a polynucleotide encoding a full-length polypeptide as shown in SEQ II) NO:6.

18. The method of claim 15, wherein the plant is a dicotyledonous plant.

19. The method of claim 15, wherein the plant is a monocotyledonous plant.

20. The method of claim 15, wherein the plant is selected from the group consisting of rapeseed, canola, linseed, soybean, sunflower, maize, oat, rye, barley, wheat, pepper, tagetes, cotton, oil palm, coconut palm, flax, castor and peanut.

21. A method of increasing the amount of a lipid in a plant comprising the step of increasing the expression of a Lipid Metabolism Regulator (LMR) nucleic acid in the plant, wherein the LMR nucleic acid is selected from the group consisting of:
 a) a full-length polynucleotide as shown in SEQ ID NO:4;
 b) a full-length polynucleotide as shown in SEQ ID NO:5;
 c) a polynucleotide encoding a Mi-length polypeptide as shown in SEQ ID NO:6;
 d) a polynucleoticle having at least 95% sequence identity with the polynucleotidc of any of a) through b) above;
 e) a polynucleotide encoding a polypeptide having at least 95% sequence identity with the polypeptide of e) above; and
 f) a polynucleotide complementary to a full-length polynucleotide of any of a) though e) above;

wherein expression of the LMR nucleic acid in a plant results in an increased level of a lipid in the plant as compared to a control plant, and wherein the control plant has not been transformed with the LMR nucleic acid.

22. The method of claim 21, wherein the LMR nucleic acid comprises a full-length polynucleotide as shown in SEQ ID NO:4.

23. The method of claim 21, wherein the LMR nucleic acid comprises a polynucleotide encoding a full-length polypeptide as shown in SEQ ID NO:6.

24. The method of claim 21, wherein the plant is a dicotyledonous plant.

25. The method of claim 21, wherein the plant is a monocotyledonous plant.

26. The method of claim 21, wherein the plant is selected from the group consisting of rapeseed, canola, linseed, soybean, sunflower, maize, oat, rye, barley, wheat, pepper, tagetes, cotton, oil palm, flax, castor and peanut.

* * * * *

UNITED STATES PATENT AND TRADEMARK OFFICE
CERTIFICATE OF CORRECTION

PATENT NO. : 7,230,160 B2  
APPLICATION NO. : 10/094458  
DATED : June 12, 2007  
INVENTOR(S) : Christoph Benning et al.

Page 1 of 1

It is certified that error appears in the above-identified patent and that said Letters Patent is hereby corrected as shown below:

In Claim 14, in column 70, on line 46, "14. A seed produced by the trausgenic plant of claim 13," should read -- 14. A seed produced by the transgenic plant of claim 13, --.

In Claim 17, in column 71, line 12, "polypeptide as shown in SEQ II) NO:6." should read -- polypeptide as shown in SEQ ID NO:6. --

In Claim 21, in column 71, on line 29, "c) a polynucleotide encoding a Mi-length polypeptide as" should read -- c) a polynucleotide encoding a full-length polypeptide as --.

In Claim 21, in column 72, on line 4, "95% sequence identity with the polypeptide of e)" should read -- 95% sequence identity with the polypeptide of c) --.

Signed and Sealed this

Fifteenth Day of April, 2008

JON W. DUDAS  
*Director of the United States Patent and Trademark Office*

```
                          SEQUENCE LISTING

<160> NUMBER OF SEQ ID NOS: 39

<210> SEQ ID NO 1
<211> LENGTH: 1539
<212> TYPE: DNA
<213> ORGANISM: Arabidopsis thaliana

<400> SEQUENCE: 1
aaaccactct gcttcctctt cctctgagaa atcaaatcac tcacactcca aaaaaaaatc     60
taaactttct cagagtttaa tgaagaagcg cttaaccact tccacttgtt cttcttctcc    120
atcttcctct gtttcttctt ctactactac ttcctctcct attcagtcgg aggctccaag    180
gcctaaacga gccaaaaggg ctaagaaatc ttctccttct ggtgataaat ctcataaccc    240
gacaagccct gcttctaccc gacgcagctc tatctacaga ggagtcacta gacatagatg    300
gactgggaga ttcgaggctc atctttggga caaaagctct tggaattcga ttcagaacaa    360
gaaaggcaaa caagtttatc tgggagcata tgacagtgaa gaagcagcag cacatacgta    420
cgatctggct gctctcaagt actggggacc cgacaccatc ttgaattttc cggcagagac    480
gtacacaaag gaattggaag aaatgcagag agtgacaaag gaagaatatt tggcttctct    540
ccgccgccag agcagtggtt tctccagagg cgtctctaaa tatcgcggcg tcgctaggca    600
tcaccacaac ggaagatggg aggctcggat cggaagagtg tttgggaaca agtacttgta    660
cctcggcacc tataatacgc aggaggaagc tgctgcagca tatgacatgg ctgcgattga    720
gtatcgaggc gcaaacgcgg ttactaattt cgacattagt aattacattg accggttaaa    780
gaagaaaggt gttgtcccgt tccctgtgaa ccaagctaag gatcaagagg gtattcttgt    840
tgaagccaaa caagaagttg aaacgagaga agcgaaggaa gagcctagag aagaagtgaa    900
acaacagtac gtggaagaac caccgcaaga agaagaagag aaggaagaag agaaagcaga    960
gcaacaagaa gcagagattg taggatattc agaagaagca gcagtggtca attgctgcat   1020
agactcttca accataatgg aaatggatcg ttgtggggac aacaatgagc tggcttggaa   1080
cttctgtatg atggatactg ggttttctcc gtttttgact gatcagaatc tcgcgaatga   1140
gaatcccata gagtatccgg agctattcaa tgagttagca tttgaggaca acatcgactt   1200
catgttcgat gatgggaagc acgagtgctt gaacttggaa aatctggatt gttgcgtggt   1260
gggaagagag agcccaccct cttcttcttc accattgtct tgcttatcta ctgactctgc   1320
ttcatcaaca acaacaacaa caacctcggt ttcttgtaac tatttggtct gagagagaag   1380
agctttgcct tctagtttga atttctattt cttccgcttc ttcttctttt ttttcttttg   1440
ttgggttctg cttagggttt gtatttcagt ttcagggctt gttcgttggt tctgaataat   1500
caatgtcttt gcccctttc taatgctcca agttcagat                            1539

<210> SEQ ID NO 2
<211> LENGTH: 1293
<212> TYPE: DNA
<213> ORGANISM: Arabidopsis thaliana

<400> SEQUENCE: 2
atgaagaagc gcttaaccac ttccacttgt tcttcttctc catcttcctc tgtttcttct     60
```

-continued

```
tctactacta cttcctctcc tattcagtcg gaggctccaa ggcctaaacg agccaaaagg      120
gctaagaaat cttctccttc tggtgataaa tctcataacc cgacaagccc tgcttctacc      180
cgacgcagct ctatctacag aggagtcact agacatagat ggactgggag attcgaggct      240
catctttggg acaaaagctc ttggaattcg attcagaaca agaaaggcaa acaagtttat      300 ctggagcat atgacagtga agaagcagca gcacatacgt acgatctggc tgctctcaag       360
tactggggac ccgacaccat cttgaatttt ccggcagaga cgtacacaaa ggaattggaa      420
gaaatgcaga gagtgacaaa ggaagaatat ttggcttctc tccgccgcca gagcagtggt      480
ttctccagag gcgtctctaa atatcgcggc gtcgctaggc atcaccacaa cggaagatgg      540
gaggctcgga tcggaagagt gtttgggaac aagtacttgt acctcggcac ctataatacg      600
caggaggaag ctgctgcagc atatgacatg gctgcgattg agtatcgagg cgcaaacgcg      660
gttactaatt tcgacattag taattacatt gaccggttaa agaagaaagg tgttgtcccg      720
ttccctgtga accaagctaa ggatcaagag ggtattcttg ttgaagccaa acaagaagtt      780
gaaacgagag aagcgaagga agagcctaga aagaagtgaa acaacagta cgtggaagaa       840 ccaccgcaag aagaagaaga aaggaagaa gagaaagcag agcaacaaga agcagagatt       900
gtaggatatt cagaagaagc agcagtggtc aattgctgca tagactcttc aaccataatg      960
gaaatggatc gttgtgggga caacaatgag ctggcttgga acttctgtat gatggatact     1020
gggttttctc cgtttttgac tgatcagaat ctcgcgaatg agaatcccat agagtatccg     1080
gagctattca atgagttagc atttgaggac aacatcgact tcatgttcga tgatgggaag     1140
cacgagtgct tgaacttgga aaatctggat tgttgcgtgg tgggaagaga gagcccaccc     1200
tcttcttctt caccattgtc ttgcttatct actgactctg cttcatcaac aacaacaaca     1260
acaacctcgg tttcttgtaa ctatttggtc tga                                  1293
```

<210> SEQ ID NO 3
<211> LENGTH: 430
<212> TYPE: PRT
<213> ORGANISM: Arabidopsis thaliana

<400> SEQUENCE: 3

```
Met Lys Lys Arg Leu Thr Thr Ser Thr Cys Ser Ser Pro Ser Ser
 1               5                  10                  15

Ser Val Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
                100                 105                 110

Thr Tyr Asp Leu Ala Ala Leu Lys Tyr Trp Gly Pro Asp Thr Ile Leu
            115                 120                 125

Asn Phe Pro Ala Glu Thr Tyr Thr Lys Glu Leu Glu Glu Met Gln Arg
        130                 135                 140

Val Thr Lys Glu Glu Tyr Leu Ala Ser Leu Arg Arg Gln Ser Ser Gly
```

```
                145                 150                 155                 160
Phe Ser Arg Gly Val Ser Lys Tyr Arg Gly Val Ala Arg His His His
                    165                 170                 175
Asn Gly Arg Trp Glu Ala Arg Ile Gly Arg Val Phe Gly Asn Lys Tyr
                180                 185                 190
Leu Tyr Leu Gly Thr Tyr Asn Thr Gln Glu Glu Ala Ala Ala Ala Tyr
            195                 200                 205
Asp Met Ala Ala Ile Glu Tyr Arg Gly Ala Asn Ala Val Thr Asn Phe
        210                 215                 220
Asp Ile Ser Asn Tyr Ile Asp Arg Leu Lys Lys Lys Gly Val Val Pro
225                 230                 235                 240
Phe Pro Val Asn Gln Ala Lys Asp Gln Glu Gly Ile Leu Val Glu Ala
                245                 250                 255
Lys Gln Glu Val Glu Thr Arg Glu Ala Lys Glu Glu Pro Arg Glu Glu
                260                 265                 270
Val Lys Gln Gln Tyr Val Glu Glu Pro Pro Gln Glu Glu Glu Glu Lys
            275                 280                 285
Glu Glu Glu Lys Ala Glu Gln Gln Glu Ala Glu Ile Val Gly Tyr Ser
        290                 295                 300
Glu Glu Ala Ala Val Val Asn Cys Cys Ile Asp Ser Ser Thr Ile Met
305                 310                 315                 320
Glu Met Asp Arg Cys Gly Asp Asn Asn Glu Leu Ala Trp Asn Phe Cys
                325                 330                 335
Met Met Asp Thr Gly Phe Ser Pro Phe Leu Thr Asp Gln Asn Leu Ala
                340                 345                 350
Asn Glu Asn Pro Ile Glu Tyr Pro Glu Leu Phe Asn Glu Leu Ala Phe
            355                 360                 365
Glu Asp Asn Ile Asp Phe Met Phe Asp Asp Gly Lys His Glu Cys Leu
        370                 375                 380
Asn Leu Glu Asn Leu Asp Cys Cys Val Val Gly Arg Glu Ser Pro Pro
385                 390                 395                 400
Ser Ser Ser Ser Pro Leu Ser Cys Leu Ser Thr Asp Ser Ala Ser Ser
                405                 410                 415
Thr Thr Thr Thr Thr Thr Ser Val Ser Cys Asn Tyr Leu Val
                420                 425                 430

<210> SEQ ID NO 4
<211> LENGTH: 1465
<212> TYPE: DNA
<213> ORGANISM: Arabidopsis thaliana

<400> SEQUENCE: 4
ttggtaccaa atctaaactt tctcagagtt taatgaagaa gcgcttaacc acttccactt      60
gttcttcttc tccatcttcc tctgtttctt cttctactac tacttcctct cctattcagt     120
cggaggctcc aaggcctaaa cgagccaaaa gggctaagaa atcttctcct tctggtgata     180
aatctcataa cccgacaagc cctgcttcta cccgacgcag ctctatctac agaggagtca     240
ctagacatag atggactggg agattcgagg ctcatctttg ggacaaaagc tcttggaatt     300
cgattcagaa caagaaaggc aaacaagttt atctgggagc atatgacagt gaagaagcag     360
cagcacatac gtacgatctg ctgctctca agtactgggg acccgacacc atcttgaatt      420
ttccggcaga gacgtacaca aaggaattgg aagaaatgca gagagtgaca aaggaagaat     480
atttggcttc tctccgccgc cagagcagtg gtttctccag aggcgtctct aaatatcgcg     540
```

| | |
|---|---|
| gcgtcgctag gcatcaccac aacggaagat gggaggctcg gatcggaaga gtgtttggga | 600 |
| acaagtactt gtacctcggc acctataata cgcaggagga agctgctgca gcatatgaca | 660 |
| tggctgcgat tgagtatcga ggcgcaaacg cggttactaa tttcgacatt agtaattaca | 720 |
| ttgaccggtt aaagaagaaa ggtgtttttcc cgttccctgt gaaccaagct aaccatcaag | 780 |
| agggtattct tgttgaagcc aaacaagaag ttgaaacgag agaagcgaag gaagagccta | 840 |
| gagaagaagt gaaacaacag tacgtggaag aaccaccgca agaagaagaa gagaaggaag | 900 |
| aagagaaagc agagcaacaa gaagcagaga ttgtaggata ttcagaagaa gcagcagtgg | 960 |
| tcaattgctg catagactct tcaaccataa tggaaatgga tcgttgtggg gacaacaatg | 1020 |
| agctggcttg gaacttctgt atgatggata cagggttttc tccgttttg actgatcaga | 1080 |
| atctcgcgaa tgagaatccc atagagtatc cggagctatt caatgagtta gcatttgagg | 1140 |
| acaacatcga cttcatgttc gatgatggga agcacgagtg cttgaacttg gaaaatctgg | 1200 |
| attgttgcgt ggtgggaaga gagagcccac cctcttcttc ttcaccattg tcttgcttat | 1260 |
| ctactgactc tgcttcatca acaacaacaa caacaacctc ggtttcttgt aactatttgg | 1320 |
| tctgagagag agagctttgc cttctagttt gaatttctat ttcttccgct tcttcttctt | 1380 |
| ttttttcttt tgttgggttc tgcttagggt ttgtatttca gtttcagggc ttgttcgttg | 1440 |
| gttctgaata atcaatgtct ttgcc | 1465 |

<210> SEQ ID NO 5
<211> LENGTH: 1293
<212> TYPE: DNA
<213> ORGANISM: Arabidopsis thaliana

<400> SEQUENCE: 5

| | |
|---|---|
| atgaagaagc gcttaaccac ttccacttgt tcttcttctc catcttcctc tgtttcttct | 60 |
| tctactacta cttcctctcc tattcagtcg gaggctccaa ggcctaaacg agccaaaagg | 120 |
| gctaagaaat cttctccttc tggtgataaa tctcataacc cgacaagccc tgcttctacc | 180 |
| cgacgcagct ctatctacag aggagtcact agacatagat ggactgggag attcgaggct | 240 |
| catctttggg acaaaagctc ttggaattcg attcagaaca agaaaggcaa acaagtttat | 300 |
| ctggagcat atgacagtga agaagcagca gcacatacgt acgatctggc tgctctcaag | 360 |
| tactggggac ccgacaccat cttgaatttt ccggcagaga cgtacacaaa ggaattggaa | 420 |
| gaaatgcaga gagtgacaaa ggaagaatat ttggcttctc tccgccgcca gagcagtggt | 480 |
| ttctccagag gcgtctctaa atatcgcggc gtcgctaggc atcaccacaa cggaagatgg | 540 |
| gaggctcgga tcggaagagt gtttgggaac aagtacttgt acctcggcac ctataatacg | 600 |
| caggaggaag ctgctgcagc atatgacatg gctgcgattg agtatcgagg cgcaaacgcg | 660 |
| gttactaatt tcgacattag taattacatt gaccggttaa agaagaaagg tgttttcccg | 720 |
| ttccctgtga accaagctaa ccatcaagag gtattcttg ttgaagccaa acaagaagtt | 780 |
| gaaacgagag aagcgaagga agagcctaga agaagtgta acaacagta cgtggaagaa | 840 |
| ccaccgcaag aagaagaga aggaagaa gagaaagcag agcaacaaga agcagagatt | 900 |
| gtaggatatt cagaagaagc agcagtggtc aattgctgca tagactcttc aaccataatg | 960 |
| gaaatggatc gttgtgggga caacaatgag ctggcttgga acttctgtat gatggataca | 1020 |
| gggttttctc cgttttgac tgatcagaat ctcgcgaatg agaatcccat agagtatccg | 1080 |
| gagctattca atgagttagc atttgaggac aacatcgact tcatgttcga tgatgggaag | 1140 |
| cacgagtgct tgaacttgga aaatctggat tgttgcgtgg tgggaagaga gagcccaccc | 1200 |

```
tcttcttctt caccattgtc ttgcttatct actgactctg cttcatcaac aacaacaaca   1260
acaacctcgg tttcttgtaa ctatttggtc tga                                1293
```

<210> SEQ ID NO 6
<211> LENGTH: 430
<212> TYPE: PRT
<213> ORGANISM: Arabidopsis thaliana

<400> SEQUENCE: 6

```
Met Lys Lys Arg Leu Thr Thr Ser Thr Cys Ser Ser Ser Pro Ser Ser
 1               5                  10                  15

Ser Val Ser Ser Thr Thr Thr Ser Ser Pro Ile Gln Ser Glu Ala
             20                  25                  30

Pro Arg Pro Lys Arg Ala Lys Arg Ala Lys Lys Ser Ser Pro Ser Gly
         35                  40                  45

Asp Lys Ser His Asn Pro Thr Ser Pro Ala Ser Thr Arg Arg Ser Ser
     50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Gln Asn Lys Lys Gly
                 85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350
```

```
Asn Glu Asn Pro Ile Glu Tyr Pro Glu Leu Phe Asn Glu Leu Ala Phe
            355                 360                 365
Glu Asp Asn Ile Asp Phe Met Phe Asp Asp Gly Lys His Glu Cys Leu
        370                 375                 380
Asn Leu Glu Asn Leu Asp Cys Cys Val Val Gly Arg Glu Ser Pro Pro
385                 390                 395                 400
Ser Ser Ser Ser Pro Leu Ser Cys Leu Ser Thr Asp Ser Ala Ser Ser
                405                 410                 415
Thr Thr Thr Thr Thr Thr Ser Val Ser Cys Asn Tyr Leu Val
                420                 425                 430

<210> SEQ ID NO 7
<211> LENGTH: 10140
<212> TYPE: DNA
<213> ORGANISM: Arabidopsis thaliana

<400> SEQUENCE: 7
```

| | | | | | |
|---|---|---|---|---|---|
| aagcttcaat | atgattcact | taaaatgtgg | taagtagggg | agatgaaaag | gacttatctt | 60 |
| atagaaattg | agtcgtttat | tttgttggtc | caccatacat | ttacatgaaa | tggttacatc | 120 |
| aggacgagtg | ttgtctgaga | cctagaaaat | cagaaaccaa | aaccacaaaa | gaattaaaat | 180 |
| gaaattacag | acacaatcat | gaatctctaa | cataagaaat | aacaaaacca | ccttcacgtg | 240 |
| atacaactct | ttggtttctt | caacacaaaa | tcccattttg | tgtacagctc | tatacccaac | 300 |
| attttcgaca | taagactttg | ggacatttgt | acgaaacatt | tcttcaatt | ctccaaagt | 360 |
| gcttttagtt | aacggaccat | ctcttagagt | tcctgatgaa | ctaacactgc | atcaatttga | 420 |
| taagataaca | atcggtaaac | ttgtttattc | aacataaaaa | agacttgatt | agcgagaaat | 480 |
| gcgcaatcca | actatagttt | ctaagttgtc | tagatagtag | ataaccgact | caactatagt | 540 |
| gtccaagttg | tcaacacagt | ttcaatccac | tacaaaccac | ctacggtaat | tacaatgctc | 600 |
| ttaaaccaac | actaggctaa | tcactaaccc | tgccccaggt | aaaacagagt | tgtgtgtgt | 660 |
| ccctaaaaac | tgaaaatttg | aggagaagtc | aaaaaccttta | ctcatggaaa | acaacattac | 720 |
| caaaccgagc | gatcagtctg | agtttgacat | cctctgatcc | accataaccct | agcaacgtct | 780 |
| tctttgccct | atcaaatccc | attataatgt | catcctccac | tttctctgtc | acccataacc | 840 |
| atggattttc | cagttttccc | aaatcactct | tcgctaagat | taccaaagat | ttttcttctg | 900 |
| cgtctttcct | ccactctgaa | gaaccgggca | aagttgaaa | gttgctatcc | tctggatccg | 960 |
| aaccaacgag | aaaccatcta | gaaatgtaac | cgtttgcgta | gattatcttt | gtattagtac | 1020 |
| tcccgacgtt | tttattgtgt | tttttaagaa | gagaaggtgg | aacagaggat | gctctcaatg | 1080 |
| caacattttc | aagtcgttta | tgtggtggaa | cgtaagacat | ctctgaaacg | aatatatgat | 1140 |
| actaggaaaa | ttaaaagctg | attccaaaaa | gataactcaa | gtttccgagc | aacgaagtat | 1200 |
| gagaagaaga | aacaaaagag | tacctttaa | ttatatcagc | ttaggtcatt | caaagaaga | 1260 |
| acgacgatca | tacgagagga | aactgaaaag | gcgcagagca | gtgaactgaa | gtggaagaga | 1320 |
| cgagacggtt | tggtctttttt | atcactagaa | gtttagtctt | ggaaatgtgc | ataatattta | 1380 |
| atttcatttc | aattttcaaa | tcaaaaaata | aaaccgataa | cgaaactctt | gttatcatat | 1440 |
| tatgagcgtt | gataatttag | agaatctctg | ttcttttaga | aaattgtatg | aacattttgt | 1500 |
| taaataaata | actatttta | aatgctaaac | ctcattgttt | agtcctaaat | gttaggaatc | 1560 |
| ttagtattca | ttttttttc | ctcttatgat | atacacttcc | ggtttagatt | tctaggacgt | 1620 |
| tttaaattta | attattactg | ctaataaaaa | tagttattta | tttttaaaca | attaaataaa | 1680 |

```
acaattgtat ctctagagta aaaaaagttt taaaaatttt ggtgaatgtt tttatttggc    1740
aacccaactt aattcctgaa acgaatcacg agaattattt aacgtactac aaaaggtaca    1800
tctaattttc taaaaccgaa ttagactatc gtcttggttg ttttttggatg ttgcatgtct   1860 atattatgat aattattctg taagcattac aattaaatcg tttctgtttt tactaaagga    1920
gttttgactg ttttaaacga ctgtaaacac tcgtgtgtct gcttaaatca tgtggaaagt    1980
taaatgataa cagttagaac atccaacttt acatatgctt tgattagaca ttttctacga    2040
tatgtttcgg attgacacgt gctaatcata tctgatcatt ttcccatttt acatatgttc    2100
taattaggca ttttcgacga tacattttag atcgataatg tgttaataat catctgacat    2160
tttttacttt gtatgttcta attatgtatt tatacgataa acattagatc gacacatgca    2220
aaacattcga caatttgttg aacactgaag acctaatttg gtataataca gctcagcgaa    2280
gatacgttac aactaatttg gagcgtttat agaaaatata ggcaaatagc caaatatgct    2340 aataaaaga tttagaactt taataggtaa tttaacacat tttataacac aaagcatat     2400 atatttaaaa gggaaaaaac tagtcaactt tcatagacca tcattaccat aataactcaa    2460
ttcaatcaaa ttttaatttt tggctactat ttttctttc taaaaccaaa acatcatcat    2520
agtagattct tcaattttaa aatatagaat tcaaattgtt gaccagggaa taaatagaat    2580
tgcaaaaaaa caaattaaga tattttacat tccaactttt cccccaaaaa attagagaaa    2640
aaaatcaaat taaattcaat aattccaaaa cataaaacgt acaaaaaagt taatgataaa    2700
aaaacgtaaa aaaaaataca aaaatacaaa gaaaaaagaa agacagcgtg gagagtaaag    2760
ctattggtag catggctgca acagaaggcc aagtgtttgg tcttacaatt tcatttttaa    2820
ctctttgtgt taattaaccc aattagccct ttcctccttc agggtttatt taacttgccc    2880
tttctcgttt cctccttttt ttcttaaacc actctgcttc ctcttcctct gagaaatcaa    2940
atcactcaca ctccaaaaaa aaatctaaac tttctcagag tttaatgaag aagcgcttaa    3000
ccacttccac ttgttcttct tctccatctt cctctgtttc ttcttctact actacttcct    3060
ctcctattca gtcggaggct ccaaggccta aacgagccaa aagggctaag aaatcttctc    3120
cttctggtga taaatctcat aacccgacaa gccctgcttc tacccgacgc agctctatct    3180
acagaggagt cactaggttt ttattttttt ggaaattaaa tgattggttg ttgagattgg    3240
atttgggttt tgtcttaaaa ctgcatttgt aagattgcat gttgttttgt gggattttgc    3300
agacatagat ggactgggag attcgaggct catctttggg acaaaagctc ttggaattcg    3360
attcagaaca agaaaggcaa acaaggtttc gtcttcttct ttttttcttc gtaactcatg    3420
attttgtttg ttttaataaa gatctggact taactgata aatttggttt ctttgatctg     3480
ttgtttgatc tcaacttcgt cacaacttca ccagtttatc tgggtaagct ctaattctct    3540
gaaacaaaag atcaattgtt ttttactaaa ttgaaagaga aaaaaaaga gagagtggat    3600 ttggtcagaa gaatctcaac tgctttcacg cgtaattgca ggagcatatg acagtgaaga    3660
agcagcagca catacgtacg atctggctgc tctcaagtac tggggacccg acaccatctt    3720
gaattttccg gtaaaccaaa aaacaaaaat cagattgttt tgatatgcat gtttgtgatt    3780
ttggaatctg gattataatt aaaaaaaaaa atggggaaaa tcaggcagag acgtacacaa    3840
aggaattgga agaaatgcag agagtgacaa aggaagaata tttggcttct ctccgccgcc    3900
agagcagtgg tttctccaga ggcgtctcta aatatcgcgg cgtcgctagg ttcctttttt    3960
tctctctttc ttttttttaat ttctttagat ttatttttta aatttcggaa tttactacca    4020
aattgagaaa tgatttttcc tattttcgga tatctgaata acagaattaa ttattaggaa    4080
```

```
aaaatctgat catgaaaatt ttgcttttag aatattctct ttttcttaaa aaaaatcata    4140
aattatgttt ttttcagcac tgctaaagtt tatggattca atagtttggt cattttattc    4200
ttaaaaatag gattatttt gttcataaaa acaggcatca ccacaacgga agatgggagg     4260
ctcggatcgg aagagtgttt gggaacaagt acttgtacct cggcacctat agtacgttat    4320
ctcctttccc ttttttcttc tagtaatttt tagaaaaaaa tagatatgta ctcttggtta    4380
atttaaaata attagcgtaa ttattgactt ttttataact taccgggcat aacggatcct    4440
ttttacctgt tatgctttat aatatataat tttgtaagta taaaatagag tgtgataatg    4500
tttagactgt tttttgttgt tgtttataag agtgatttaa gaatattaat ttgtttagtg    4560
agacaattag aataatataa tggggaagca gtggcagtgg ggtttgaatt ttacacacac    4620
tgactcacgt gaggcgagag ttttgacatc atgtcccttt aattgatttt tatcttttaa    4680
tcaaatcaac ttttttttctt cttctttttt aattatctga tccctctgca taattacctt    4740
ttaaattctg catttttgt ggatccgata ctctgaatac aaaaattgag aactctgcag     4800
aagggaatat taacaacaac tcttttactg aaaagtaatc ccatttttt ttattgtttt     4860 tgctgactct taccgggtcc ttagatttat ttaaggacct cctaatcttc aacaaatctc    4920 aaattttga aaattagatt tttttaaaaa agtaatacaa attgagattt gcaaaaatat     4980
aggcattgtt gttctataac aaagatactt tatttatacc aaaaaaaaga aaagagttgt    5040
caagagcata attacaaaaa aaaaaattga aataagtagt agttgtgaaa ttttgtatag    5100
aaaaataatg taggttacaa gtgtaaaggc gcgtgtagcg cgcgtaggtc acgtgataac    5160
actctcactt cataaaagga caaaatagtt cagagaggct ttaggaccaa acccgaggtc    5220
gatctggttt gctcttgttt ttttggttta ttaaattgga ttaattagtt agagttgaga    5280
cttgctctga gtaggagtca cgagccctca cgtgcactgc tcatctctct ctatctctct    5340
accatatctt tcatctttgt cctccgaaca aaatctggtc taactttatc ttcttttctt    5400
ttaataattg tcttctctac tttaccatta ttttctcta gattattctg gtaccaaact     5460
tataacttaa tagttgatta gtgcttagag ttgacactag gttggtgttt taattattgt    5520
taattaactc agtaatcgta cgttcgtgta ttaattatat acacaaattg ttgcgatgac    5580
ttaaattaag tcacaagttt ggactctta gtgtttagag cggcgcagtg gaggagaaat     5640
ggtctttgta cacgcctcac atctccacac aaatcgtgta accctagttg tccctacaaa    5700
aacacgtcac caaattctat tgattctttg tctttattag gtatcataaa ttctctaatt    5760
taaatatgaa acgacaaaga agaaactctt cttttaaca cttgtttggt cttatttggt     5820
tatagccact taccaggtaa tgtgaaagtt aacaacaagt tgcgttaact ttcaaaacac    5880
tgactttgtt tgcattgtct tgatttagaa gcttttagc taacacagtt gtctatttat     5940
tggttttaca gatacgcagg aggaagctgc tgcagcatat gacatggctg cgattgagta    6000
tcgaggcgca aacgcggtta ctaatttcga cattagtaat tacattgacc ggttaaagaa    6060
gaaaggtgtt ttcccgttcc ctgtgaacca agctaaccat caagagggta ttcttgttga    6120
agccaaacaa gaagttgaaa cgagagaagc gaaggaagag cctagagaag aagtgaaaca    6180
acagtacgtg gaagaaccac cgcaagaaga agaagaaag gaagaagaga agcagagca     6240 acaagaagca gagattgtag gatattcaga agaagcagca gtggtcaatt gctgcataga    6300
ctcttcaacc ataatggaaa tggatcgttg tgggacaac aatgagctgg cttggaactt     6360
ctgtatgatg gatacagggt tttctccgtt tttgactgat cagaatctcg cgaatgagaa    6420
```

-continued

```
tcccatagag tatccggagc tattcaatga gttagcattt gaggacaaca tcgacttcat    6480
gttcgatgat gggaagcacg agtgcttgaa cttggaaaat ctggattgtt gcgtggtggg    6540
aagagagagc ccaccctctt cttcttcacc attgtcttgc ttatctactg actctgcttc    6600
atcaacaaca acaacaacaa cctcggtttc ttgtaactat ttggtctgag agagagagct    6660
ttgccttcta gtttgaattt ctatttcttc cgcttcttct tctttttttt cttttgttgg    6720
gttctgctta gggtttgtat ttcagtttca gggcttgttc gttggttctg aataatcaat    6780
gtctttgccc cttttctaat gctccaagtt cagataagaa ataaaaacta aatgaaccgt    6840
aaaacacaaa ggaggctaag atgtctatga atttctctgg catatgtgca ataaggaaga    6900
gcttcaagga atcttgaact aagagaaggc ttcaaaggct agacctcttc aagttcccct    6960
gtcttattat tgaccggact atgaagtttc taggaaggtt atataggcaa aagtttattc    7020
ctaactctta attcataatt ctgattgcga tgattttggg tttgctagat agtttagtaa    7080
aagagcctta ccatccaaac ttgtgatcaa tattggtaac cgtgaacgtc ttcattaggg    7140
tgaatatttg aatatctttg ttttcgggtt acacataaca acccgaaaag ttgttgcatt    7200
tggctcggaa tacatcttgt ataaaaattt gtctttactt tttagtttg taaatcaata    7260 gtatgattgg tagtctattc gttttgtgga acaacttca atttgtattt catcagacaa    7320
tatatatgca ttcaagtaga aaatcaaatc gagtaaattt gtagcataat taagtagagt    7380
ggtcaatata ataatacgat acatgataaa agtcttgaaa acattccaca cacaataagc    7440
ctaagcacta ctgatcacac aatccatatt tctttaggct ttaaaataca taactaagaa    7500
acatgacagt ttaaggtttt agcaacacca tgccttatgt tttaagtagt tactaaataa    7560
ttagatagac aatgatggca ccagcaaacc ttttagcctt taattattca agaagatgga    7620
aggtaatgat gtcagaggca gagggtgcat gaaggccatg gttggggtaa tagtggtgat    7680
ggttctggtg gaaacgaaga gcgtaagcac gtgacccttc gatttggtat ccaagaactg    7740
agtcgtaatc tcctccattg tctactagtc catagtgagg atcttcagct cttagttcct    7800
aattcaccaa aacatgtttt aagccatatt ccacataact aaaaccaata ttattaattc    7860
gaaatgacat gacatttgat atatgattta actaggagat atttcgataa gagaatcaca    7920
agaaaacata agagtgactg atcaatctac actacatttc tagatatctt tttaactggc    7980
tccgtattcc atgaatgtat tatgcctaaa ccaacatttg agaaaaacag aaagagatat    8040
taccagctca tgtatgagat tcttttgtat gtcttgttga cttttgttct gcaattgtgt    8100
aaaccacaag agaaatgatg aagaaatatt ccctcccaaa aaaattatga agatatatac    8160
ccaagttatt atgacatcac tatatagtat acttggtatt ttctttatcc attagcttaa    8220
acacacacac acacacacaa atataattgt ccaagaaaag tgttatcaac agttttagta    8280
agttgataaa ttcaattgac acaaaattgt tgagacaaat aaatatgata aaatggaaaa    8340
gtgagtggac atagaagatg tgaccttttt cttggtggtc tcgatctgat tcccaagaga    8400
tttgaactgt acagtacaat acaattaaca tatattatcc aacagtaaac aaaatgtttc    8460
tttttctaaa acatatatac aacaataaaa ttcattttt aataattcaa ttcaaaactg    8520
aagcttgggt ataggatt aattgaaacc ctaggtaagg gaaaagtatg aagagaacct    8580
tgcgctcgcg aacgagtttg aaagtgtttt ccatttcatc ctcaagacga cgcagctcct    8640
gaatgtcaag ctcgtccaaa cactcaccta gcctctgcct acaattttaa aaatatgtat    8700
attttcgtac tcattttttt tagtaaaact cctcatctaa gagaagagag agaaacaaat    8760
acttgatctg agtccggaga tttctatttg tctccaacag tttcctcttg gtttcttgca    8820
```

-continued

```
ttcgctgcag caaaacgcat caagaattta accaaccagc gaaacacata tcaagaagaa    8880
gaagaaagat ctaagaagga aaaaaacctc atattgagtg gcccaaacat cgacatcaga    8940
aatagtttgg tacagatcta cgatctcctt cgttctataa ccaacaaaat caccaaaaaa    9000
gtagtggtta attataagaa aacaaagcaa ctcaattagc ttaatttaag agtggtgttt    9060
agagagatgg tgtacgtggt gttagggctg atatactcat gaagcttgtt ggagctagag    9120
aacatgataa tcgaaaccct agcatcacac aaaaccgtga gctcatgtgc tttcttgaat    9180
aaaccatttc ttctctttga atacgtcact tgtctgtttg tctggttctc tatcctcttg    9240
atctggatct tccctctcgc catattcttc tctctttgtt taatctttt gttgaagaga     9300 tttggtggag aggacaagag atataatgag aagaaagaag tgaaatagaa agagagagat    9360
ggagttgaag aagtaaaggg tccacttgag ttactaaaaa tggaaagtat tgcctaatcc    9420
atgaaaggta agttcagaag ttgatgaaaa ctaagtgata aattttccat ttatgtaaac    9480 tgatttttt aattacaaga cactgtttaa atcaacggac atcgatggtt gtataattac      9540 aagcactgc ttaaatcaat tgtcacttgg taaaagaggg ggaccaaagc taaaaacttg      9600
gtttgctttt cgtcaatta ttaacggagc tccgttagct tctactttgt ttttgtttag     9660
acggtgacaa acttaacggc gtttgtaaac gtcaaatcag tgcaggtgga tttggttggc    9720 ttttttacact taccctaaag taaacaaaag tgtttaggtg tgaacaagtt tttatattgg   9780
tgttaaaagc caatattcta cttttgtctg ttaatttggg aaataagaag aaagagatat    9840
atatgtttgg attaatcgtc acttccatct aactcaaatc ttttatatgt ttccccaaat    9900
gattacaata atttcccgga tttgcctta actaaagatc cttggaaaat agaatattac     9960
ccctagggtt taagaaggaa tcacaagtta ggagaaaagt ctttgtttgt agataatgtt   10020
tggtcctaac tccaaacagt ccatcaaatc agatatatga tgaaactctt ttttcttttt   10080
gcttcgacca gttagtgttg tttcaaaact aagttggcca cagttactgt tgttttgaaa   10140
```

<210> SEQ ID NO 8
<211> LENGTH: 205
<212> TYPE: PRT
<213> ORGANISM: Arabidopsis thaliana

<400> SEQUENCE: 8

```
Met Lys Lys Arg Leu Thr Thr Ser Thr Cys Ser Ser Ser Pro Ser Ser
  1               5                  10                  15

Ser Val Ser Ser Thr Thr Thr Ser Ser Pro Ile Gln Ser Glu Ala
             20                  25                  30

Pro Arg Pro Lys Arg Ala Lys Arg Ala Lys Lys Ser Ser Pro Ser Gly
         35                  40                  45

Asp Lys Ser His Asn Pro Thr Ser Pro Ala Ser Thr Arg Arg Ser Ser
     50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Gln Asn Lys Lys Gly
                 85                  90                  95

Lys Gln Gly Ala Tyr Asp Ser Glu Glu Ala Ala His Thr Tyr Asp
                100                 105                 110

Leu Ala Ala Leu Lys Tyr Trp Gly Pro Asp Thr Ile Leu Asn Phe Pro
            115                 120                 125

Ala Glu Thr Tyr Thr Lys Glu Leu Glu Glu Met Gln Arg Val Thr Lys
        130                 135                 140
```

```
Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Ser Thr Leu Ser Pro Phe Pro Phe Phe Phe
        195                 200                 205

<210> SEQ ID NO 9
<211> LENGTH: 221
<212> TYPE: PRT
<213> ORGANISM: Arabidopsis thaliana

<400> SEQUENCE: 9

Met Ala Ala Ile Glu Tyr Arg Gly Ala Asn Ala Val Thr Asn Phe Asp
1               5                   10                  15

Ile Ser Asn Tyr Ile Asp Arg Leu Lys Lys Gly Val Phe Pro Phe
            20                  25                  30

Pro Val Asn Gln Ala Asn His Gln Glu Gly Ile Leu Val Glu Ala Lys
            35                  40                  45

Gln Glu Val Glu Thr Arg Glu Ala Lys Glu Pro Arg Glu Glu Val
    50                  55                  60

Lys Gln Gln Tyr Val Glu Glu Pro Gln Glu Glu Glu Lys Glu
65                  70                  75                  80

Glu Glu Lys Ala Glu Gln Gln Glu Ala Glu Ile Val Gly Tyr Ser Glu
                85                  90                  95

Glu Ala Ala Val Val Asn Cys Cys Ile Asp Ser Ser Thr Ile Met Glu
            100                 105                 110

Met Asp Arg Cys Gly Asp Asn Asn Glu Leu Ala Trp Asn Phe Cys Met
        115                 120                 125

Met Asp Thr Gly Phe Ser Pro Phe Leu Thr Asp Gln Asn Leu Ala Asn
    130                 135                 140

Glu Asn Pro Ile Glu Tyr Pro Glu Leu Phe Asn Glu Leu Ala Phe Glu
145                 150                 155                 160

Asp Asn Ile Asp Phe Met Phe Asp Asp Gly Lys His Glu Cys Leu Asn
                165                 170                 175

Leu Glu Asn Leu Asp Cys Cys Val Val Gly Arg Glu Ser Pro Pro Ser
            180                 185                 190

Ser Ser Ser Pro Leu Ser Cys Leu Ser Thr Asp Ser Ala Ser Ser Thr
        195                 200                 205

Thr Thr Thr Thr Thr Ser Val Ser Cys Asn Tyr Leu Val
    210                 215                 220

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
acttgccctt tctcgtttc                                            19

<210> SEQ ID NO 11
<211> LENGTH: 20
<212> TYPE: DNA
```

```
<213> ORGANISM: Artificial Sequence
<220> FEATURE:
<223> OTHER INFORMATION: Description of Artificial Sequence: Primer

<400> SEQUENCE: 11
tgtttgcctt tcttgttctg                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
tggatttggg ttttgtctta                                           20

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 13
gcgtgaaagc agttgag                                              17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 14
cgaggctcat ctttggga                                             18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
tcttcctttg tcactctctg                                           20

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 16
ccgacaccat cttgaat                                              17

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
atccgagcct cccatcttcc                                           20
```

```
<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
atttcggaat ttactaccaa                                                  20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 19
caaaactctc gcctcac                                                     17

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 20
cgtctgaagg tctgcaccta ctc                                              23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
cgctaagata cttccacgtc ac                                               22

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 22
tgatggctgc gatgact                                                     17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
ttccaccata actgcgtcta                                                  20

<210> SEQ ID NO 24
<211> LENGTH: 19
<212> TYPE: DNA
<213> ORGANISM: Artificial Sequence
<220> FEATURE:
```

<223> OTHER INFORMATION: Description of Artificial Sequence: Primer

<400> SEQUENCE: 24
acttgccctt tctcgtttc                    19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
tgtttgcctt tcttgttctg                   20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 26
tgattacctg ggcacata                     18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 27
caaaagaatg cgagacaa                     18

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 28
cgctgccctt tcat                         14

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
cgcaatcctc tctctatggt                   20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
ttatacggct gggagata                     18

```
<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 31
gggcagtcaa acaggta                                                  17

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
tatctggatt cttctctggg                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
atcagggagc ttgattttgg                                               20

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
tcttggtagc atgattctca gtc                                           23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
cctttcccgc ttacagatga tc                                            22

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 36
ggtaccaaat ctaaactttc tcagag                                        26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Primer
```

```
-continued

<400> SEQUENCE: 37
actagtaaat ctaaactttc tcagag                                              26

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
tctagaaaat ctaaactttc tcagag                                              26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 39
tctagaggca aagacattga ttattc                                              26
```